(12) United States Patent
Hershoff et al.

(10) Patent No.: US 11,439,534 B2
(45) Date of Patent: Sep. 13, 2022

(54) CONTACT LENS MANIPULATOR WITH SAFETY RELEASE

(71) Applicant: Craig L. Hershoff, Sunny Isles Beach, FL (US)

(72) Inventors: Craig L. Hershoff, Sunny Isles Beach, FL (US); Andres Bernal, Sunny Isles Beach, FL (US)

(73) Assignee: Craig L. Hershoff, Sunny Isles Beach, FL (US)

( * ) Notice: Subject to any disclaimer, the term of this patent is extended or adjusted under 35 U.S.C. 154(b) by 356 days.

(21) Appl. No.: 16/634,181

(22) PCT Filed: Jul. 27, 2018

(86) PCT No.: PCT/US2018/044006
§ 371 (c)(1),
(2) Date: Jan. 27, 2020

(87) PCT Pub. No.: WO2019/023528
PCT Pub. Date: Jan. 31, 2019

(65) Prior Publication Data
US 2021/0137734 A1    May 13, 2021

Related U.S. Application Data

(60) Provisional application No. 62/621,101, filed on Jan. 24, 2018, provisional application No. 62/537,507, filed on Jul. 27, 2017.

(51) Int. Cl.
*A61F 9/00* (2006.01)
*G02C 7/04* (2006.01)
*B25J 15/06* (2006.01)

(52) U.S. Cl.
CPC .......... *A61F 9/0061* (2013.01); *B25J 15/065* (2013.01); *G02C 7/049* (2013.01)

(58) Field of Classification Search
CPC ....... A61F 9/0061; B25J 15/065; G02C 7/049
(Continued)

(56) References Cited

U.S. PATENT DOCUMENTS

| 3,424,486 A | 1/1969 | Corley |
| 3,934,914 A | 1/1976 | Carruthers |

(Continued)

FOREIGN PATENT DOCUMENTS

| KR | 10-2014-0074193 | 6/2014 |

OTHER PUBLICATIONS

Written Opinion in International Application No. PCT/US2018/044006, dated Nov. 7, 2018, pp. 1-4.

*Primary Examiner* — Dean J Kramer
(74) *Attorney, Agent, or Firm* — Saliwanchik, Lloyd & Eisenschenk

(57) ABSTRACT

The problem of inserting and removing a rigid gas permeable or hybrid contact lens is solved by the use of a lens manipulator. The lens manipulator includes a handle and an over-sleeve that is optionally attachable to an extraction stem, for creating a suction force to remove a contact lens, and an insertion stem, without suction force for placing a contact lens. Removal of the extraction stem from the over-sleeve eliminates the suction force and acts as a safety release against excessive pull force on an eye when removing a contact lens. A manual-release mechanism can be used to facilitate removal of the extraction stem.

21 Claims, 18 Drawing Sheets

(58) Field of Classification Search
USPC .......................................................... 294/1.2
See application file for complete search history.

(56) References Cited

U.S. PATENT DOCUMENTS

| | | | |
|---|---|---|---|
| 4,026,591 A | | 5/1977 | Cleaveland |
| 4,093,291 A | | 6/1978 | Schurgin |
| 4,126,345 A | * | 11/1978 | List ....................... A61F 9/0061 294/99.2 |
| 4,151,750 A | | 5/1979 | Suovaniemi et al. |
| 4,512,602 A | * | 4/1985 | England ................ A61F 9/0061 294/1.2 |
| 8,844,989 B2 | * | 9/2014 | Drake ................... A61F 9/0061 294/1.2 |
| 10,765,553 B2 | * | 9/2020 | Hershoff ................ B25J 15/065 |
| 2014/0159397 A1 | | 6/2014 | Saitoh et al. |
| 2018/0344520 A1 | * | 12/2018 | Daniels ................ A61F 9/0061 |

* cited by examiner

CONTACT LENS MANIPULATOR WITH SAFETY RELEASE

CROSS-REFERENCE TO RELATED APPLICATIONS

This application is the U.S. national stage application of International patent application No. PCT/US2018/044006, filed Jul. 27, 2018, which claims the benefit of U.S. Provisional Application Ser. No. 62/621,101, filed Jan. 24, 2018, and U.S. Provisional Application Ser. No. 62/537,507, filed Jul. 27, 2017, the disclosures of which are hereby incorporated by reference in their entireties, including all figures, tables and drawings.

BACKGROUND OF INVENTION

Contact lens wearers usually insert and remove their contact lenses manually. With Rigid Gas Permeable (RGP) and the new hybrid contact lenses this task can be more complicated. Hybrid lenses are designed to correct atypical vision problems and have irregular thicknesses, often a rigid central zone and softer peripheral zone. These types of specialized contact lenses are often larger in diameter and can form a stronger adherence to the eye surface, which can exacerbate difficult removal. Inserting and removing contact lenses can have other ergonomic limitations, given that it is a maneuver that typically requires manual dexterity, coordination, and stability. People for whom inserting and removing a RGP and hybrid contact lenses with the fingers can be a difficult task includes seniors, children, superior-limb handicapped individuals, those with long fingernails, or anyone lacking the necessary manual dexterity or stability.

A variety of lens manipulators with suction cups have been developed to manipulate specialized contact lens, but many are not equally effective for both insertion and removal of a contact lens. If the suction cup of the lens manipulator can provide sufficient suction on contact with the contact lens to facilitate removal, that same force may not release the contact lens when the suction cup is retracted. Likewise, if suction or adherence is sufficient to facilitate insertion and easy release, then the suction cup may not exert sufficient suction to be effective for removal.

Some lens manipulators utilize suction cups that rely on "passive" vacuum force, wherein the vacuum force in the cup depends upon the volume of air displacement inside the concave surface of the suction cup. Air displacement can be accomplished by either pressing the suction cup onto a surface to compress the suction cup, or by pressing/releasing a flexible or pliant bulb attached to the suction cup. Either method results in a decrease in pressure under the suction cup. These techniques, usually manually controlled, may not provide sufficient control over the vacuum force that the cup can exert on the contact lens and the eye. In other words, the amount of pressure the suction cup cannot be precisely regulated and maintained. Further, if the contact lens is stuck to the eye and cannot be removed normally, it can be difficult to disengage the already attached suction cup from the contact lens.

There is a need for a lens manipulator that can aid in inserting and removing contact lenses with more control over the amount of suction force. Such a device can, ideally, reduce the amount of manual dexterity and coordination required to remove and insert specialized contact lenses, and inhibits undesirable contact with the cornea or sclera of the eye. It can also be advantageous if the device can be released by a user through activation of a quick-release mechanism or to release the contact lens automatically if excessive extraction force is applied to the contact lens.

BRIEF SUMMARY

In accordance with the invention, the problem of inserting and extracting a contact lens from the surface of an eye is solved by a lens manipulator with a suction cup that can advantageously adjust the amount of suction force exerted by the suction cup of the lens manipulator can facilitate release of the contact lens by inhibiting the suction cup from remaining attached to the contact lens during an insertion procedure. The lens manipulator also has the ability to automatically release the suction force exerted by the suction cup, usually during an extraction procedure, if excessive force is applied to the suction cup. This release of the suction cup from the lens manipulator also causes the suction cup to release from a contact lens that is too firmly attached to the eye. The lens manipulator can also be used to release the suction cup voluntarily by the user if desired.

Suction cups have a conical, semi-circular, or similarly concave shape and are made of a malleable material that can flatten when the apex is pressed against an object, but is biased to return to the original shape. The suction force generated by a suction cup is dependent upon both the difference in air pressure between the outside and inside of the cup and the surface area under the cup. If either one of these factors is increased or decreased, it can affect the amount of suction force produced by the suction cup.

In one general embodiment, a lens manipulator has an over-sleeve with a suction cup at the proximal end and a lumen through the longitudinal length of the over-sleeve. At the proximal end, the lumen terminates in a pore that opens into the suction cup. The opposite or distal end of the lumen is placed over an adjustment rod. The combination of the lumen and the adjustment rod therein provides control over the amount of suction strength that can be formed under the suction cup. By moving the adjustment rod into or out of the lumen, the air pressure that can be generated under the suction cup can be increased or decreased, as needed. Advantageously, if the adjustment rod is removed from the lumen, such that ambient air can intrude through the lumen, the force under the suction cup is entirely released. This can inhibit excessive or damaging force being applied to a contact lens that may be stuck to the eye. The over-sleeve and adjustment rod can be configured so that the rod is pulled from the lumen if a predetermined maximum amount of pulling force is applied. Further embodiments can include a cuff that further aids in providing friction against the over-sleeve to control movement of the rod in the lumen. Still another embodiment includes a finger slide that can be used to manually release the suction cup from the adjustment rod.

When installing a contact lens on the eye, the suction cup can he directed upwards and the contact lens can be placed on the suction cup, without the application of force that would cause the suction cup to stick to the contact lens. The concavity of the contact lens can then be filled with saline or other contact lens solution. Bending forward to bring the eye into proximity with the suction cup causes the eye surface to contact the lens solution, thereby pulling the contact lens away from the suction cup and onto the eye surface.

In another embodiment, the lens manipulator has dual adjustment rods. The first adjustment rod is configured with a vented barb that removably retains the over-sleeve on the adjustment rod and inhibits the formation of suction force under the suction cup when a contact lens is placed thereon.

The second adjustment rod is configured with a finger slide mechanism that allows the over-sleeve to be manually removed from the It should be noted that this Brief Summary is provided to generally introduce the reader to one or more select concepts described below in the Detailed Disclosure in a simplified form. This Summary is not intended to identify key and/or required features of the claimed subject matter. Other aspects and further scope of applicability of the present invention will also become apparent from the detailed descriptions given herein. It should be understood, however, that the detailed descriptions, while indicating preferred embodiments of the invention, are given by way of illustration only, since various changes and modifications within the spirit and scope of the invention will become apparent from such descriptions. The invention is defined by the claims below.

BRIEF DESCRIPTION OF DRAWINGS

In order that a more precise understanding of the above recited invention can be obtained, a more particular description of the invention briefly described above will be rendered by reference to specific embodiments thereof that are illustrated in the appended drawings. The drawings presented herein may not be drawn to scale and any reference to dimensions in the drawings or the following description is specific to the embodiments disclosed. Any variations of these dimensions that will allow the subject invention to function for its intended purpose are considered to be within the scope of the subject invention. Thus, understanding that these drawings depict only typical embodiments of the invention and are not therefore to be considered as limiting in scope, the invention will be described and explained with additional specificity and detail through the use of the accompanying drawings in which:

FIG. 5A is an embodiment of a completely assembled lens manipulator. FIG. 5B is an embodiment of a lens manipulator without the over-sleeve. FIG. 5C is an embodiment of a lens manipulator without the suction cup.

FIG. 15 is a side elevation view showing the vent along the longitudinal length. FIGS. 16, 17, and 18 are a rear perspective, a front perspective, and a left side perspective view, respectively.

FIG. 19 shows the extraction stem with the fingers-slide fully retracted. FIG. 20 shows an over-sleeve disposed on the extraction stem with the finger-slide retracted. FIG. 21 shows a finger-slide pushed towards and over the extraction stem to remove the over-sleeve from the extraction stem.

In FIG. 22A, the extraction stem is shown with an over-sleeve disposed thereon. In FIG. 22B, the extraction stem and insert stem are shown with an over-sleeve disposed thereon.

DETAILED DISCLOSURE

Figure 1:
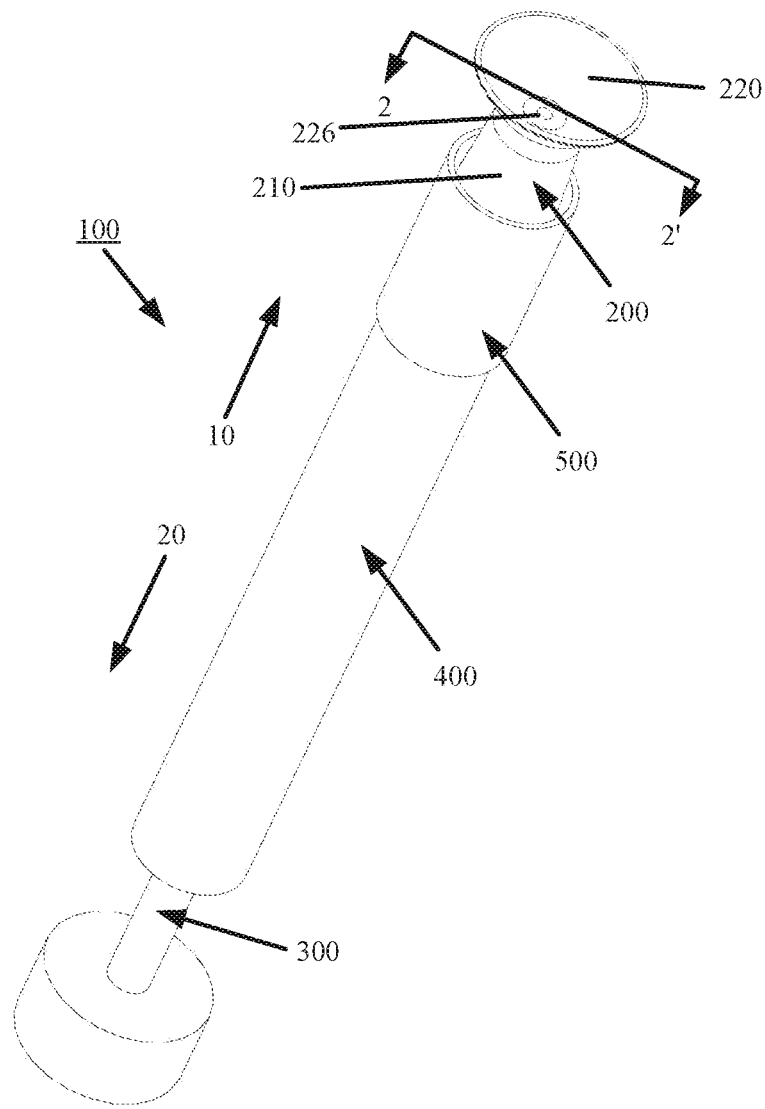
FIG. 1 is an illustration of a lens manipulator, according to an embodiment of the subject invention.

The subject invention pertains to devices and methods for inserting and removing a contact lens from the surface of an eye. More specifically, the subject invention provides one or more embodiments of a lens manipulator for use in inserting and removing Rigid Gas Permeable (RGP) and Hybrid contact lenses from the surface of an eye. Lens manipulator embodiments of the subject invention employ a suction cup to hold or secure a contact lens. Advantageously, the amount of suction force exerted onto a contact lens by a lens manipulator of the subject invention can be adjusted to the needs of a user. If the maximum pulling force of the suction cup on the lens manipulator is exceeded, in other words, there is too strong a suction force on the contact lens, a safety release mechanism can inhibit the application of a pulling force on the eye that exceeds the maximum pulling force of the lens manipulator when extracting a contact lens. The safety release mechanism can be adjusted to be activated automatically during use or configured to be intentionally activated by a user to release the suction cup from a contact lens. While embodiments of the subject invention are particularly useful with Rigid Gas Permeable (RGP) and newer hybrid lenses, a person with skill in the art will recognize the embodiments that can be utilized with other types of contact lenses.

The terms "contact" and "contact lens" are used herein for literary convenience. The devices and methods of the subject invention are particularly suited for use with RGP and with hybrid contact lenses with a rigid or semi-rigid center portion and a softer, more pliable outer ring portion. This does not preclude the embodiments herein, or variations thereof, being useful for other types of contact lenses.

The term "pull force" is used herein to refer to the amount of force applied to a suction cup to release attachment of the suction cup to a surface, such as a contact lens. A pull force can be applied in a direction away from the concavity of the suction cup or away from the surface to which the suction cup is attached.

Likewise, the term "maximum pull force" is used herein to refer to a maximum amount of force that can be applied to a suction cup of an over-sleeve of the subject invention before the over-sleeve disengages or is removed from an adjustment rod on the lens manipulator. Thus, exceeding the maximum pull force will result in the suction under the suction cup being released by removal of the adjustment rod from the lumen of the lens manipulator. A maximum pull force can be applied in a direction away from the concavity of the suction cup or away from the surface to which the suction cup is attached.

Also, as used herein, and unless otherwise specifically stated, the terms "operable communication," "operable connection," "operably connected," "cooperatively engaged" and grammatical variations thereof mean that the particular elements are connected in such a way that they cooperate to achieve their intended function or functions. The "connection" or "engagement" may be direct or indirect, physical or remote.

As used herein, the terms "longitude" or "longitudinal length" refer to the longitudinal measurement, direction, or the distance extending along the long axis of a structure or feature. For example, the longitude or longitudinal length of a lens manipulator is the distance or direction between the proximal end and the distal end. Likewise, the longitudinal length of a stem is the distance or direction between the proximal end and distal end of the stem.

Finally, reference is made throughout the application to the "proximal end" or "proximal direction" and "distal end" or "distal direction." As used herein, the proximal end or proximal direction is that end that approaches or is nearest to the eye. For example, the suction cup is at the proximal end of the lens manipulator. Conversely, the distal end or distal direction of the device is that end which approaches or is nearest to the hand during use. For example, ergonomic structures, such as a handle, for holding the lens manipulator with the fingers or hand can be located or be directed at the distal end of the lens manipulator.

It is to be understood that the figures and descriptions of embodiments of the present invention have been simplified to illustrate elements that are relevant for a clear understanding of the invention, while eliminating, for purposes of clarity, other elements that may be well known. Those of ordinary skill in the art will recognize that other elements may be desirable and/or required in order to implement the present invention. However, because such elements are well known in the art, and because they do not facilitate a better understanding of the present invention, a discussion of such elements is not provided herein.

The present invention is more particularly described in the following examples that are intended to be illustrative only because numerous modifications and variations therein will be apparent to those skilled in the art. As used in the specification and in the claims, the singular for "a," "an" and "the" include plural referents unless the context clearly dictates otherwise.

Reference will be made to the attached figures on which the same reference numerals are used throughout to indicate the same or similar components. With reference to the attached figures, which show certain embodiments of the subject invention, it can be seen that the subject invention, in general, comprises a lens manipulator 100 that includes an elongated over-sleeve 200 with a suction cup 220 at the proximal end 10 and a lumen 224 through the longitudinal length 50. The lumen opens into a pore 226 within the suction cup at the proximal end 10 and terminates at the opposite distal end 20 in a rod opening 230. A lens manipulator further comprises an adjustment rod 300 having a proximal end that is movably or slidably inserted into the rod opening. The adjustment rod can be moved into and out of the lumen to control the maximum amount of suction force generated under the suction cup. If the rod is removed from the lumen, the suction cup can be inhibited from generating a suction force, which provides an advantageous safety release feature to the lens manipulator. Additional embodiments can include an outer cuff 500 that goes around the over-sleeve to provide friction against the over-sleeve and further control over the amount of pulling force necessary to remove the over-sleeve from the adjustment rod. An alternative embodiment utilizes a dual-stem configuration. This embodiment has an insertion stem 700 and an extraction stem 800 for inserting a contact lens and extracting or removing a contact lens, respectively. In a particular embodiment, the same over-sleeve can be used on either stem. Each of these general components can have one or more sub-components, which will be discussed in detail below.

In FIG. 1 there is shown an embodiment of a lens manipulator and the various general, components thereof. In this embodiment, the over-sleeve 200 has an elongated tube portion 210 that terminates in a suction cup 220 at the proximal end 10. The suction cup can be formed as part of the tube portion to form the over-sleeve. Alternatively, the suction cup can be a separate component that is operably attached to tube portion to form the over-sleeve. In one embodiment, the suction cup is centered over the proximal end of the tube portion, such that the apex 222 or the point furthest from the outer edge, of the suction cup is aligned with the longitude 50 of the over-sleeve, such as shown, for example, in FIG. 2. In alternative embodiments, the suction cup can be off-set, such that the apex is off-center from the longitude. A person with skill in the art will be able to determine an appropriate off-set distance for the apex, to facilitate contact with a contact lens.

Figure 2:
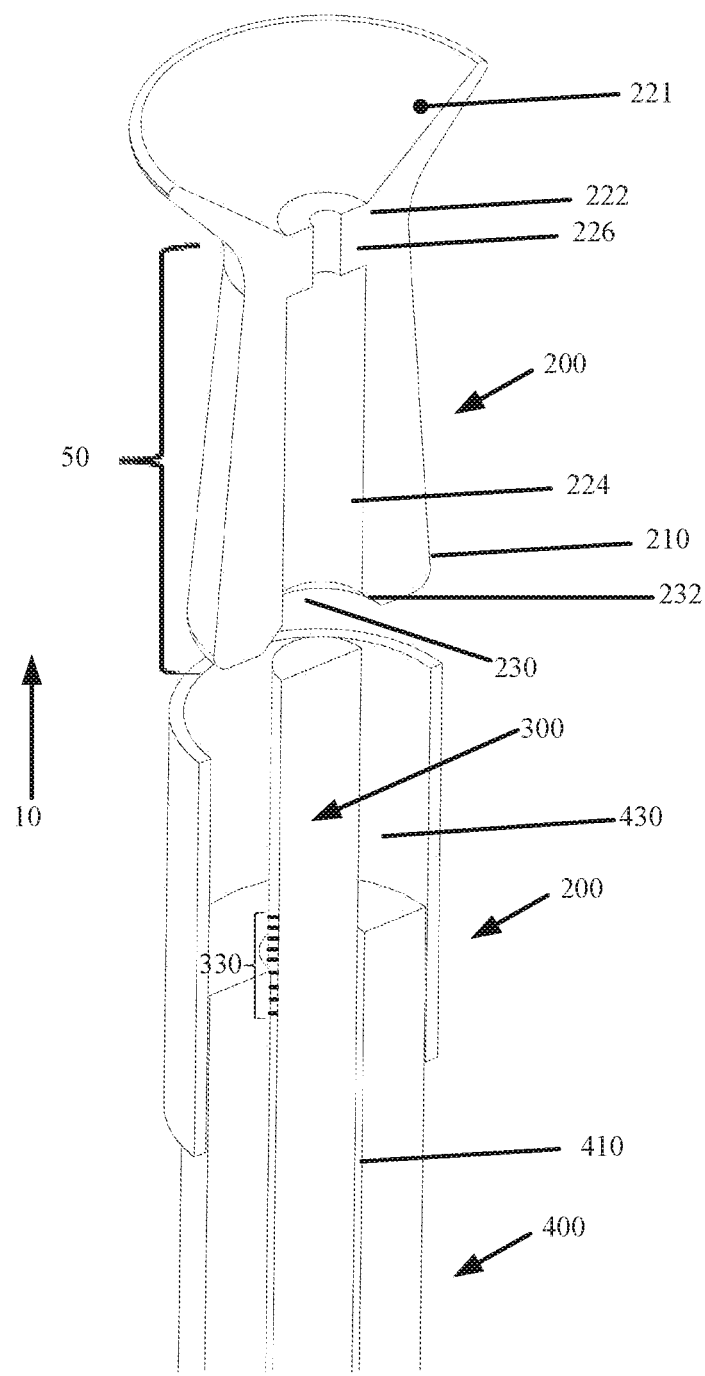
FIG. 2 is an enlarged cut-away view, taken along line 2-2' of the distal end of an embodiment of a lens manipulator, according to the subject invention. In this view, the over-sleeve is shown pulled off of the adjustment rod.
Figures 3A, 3B:
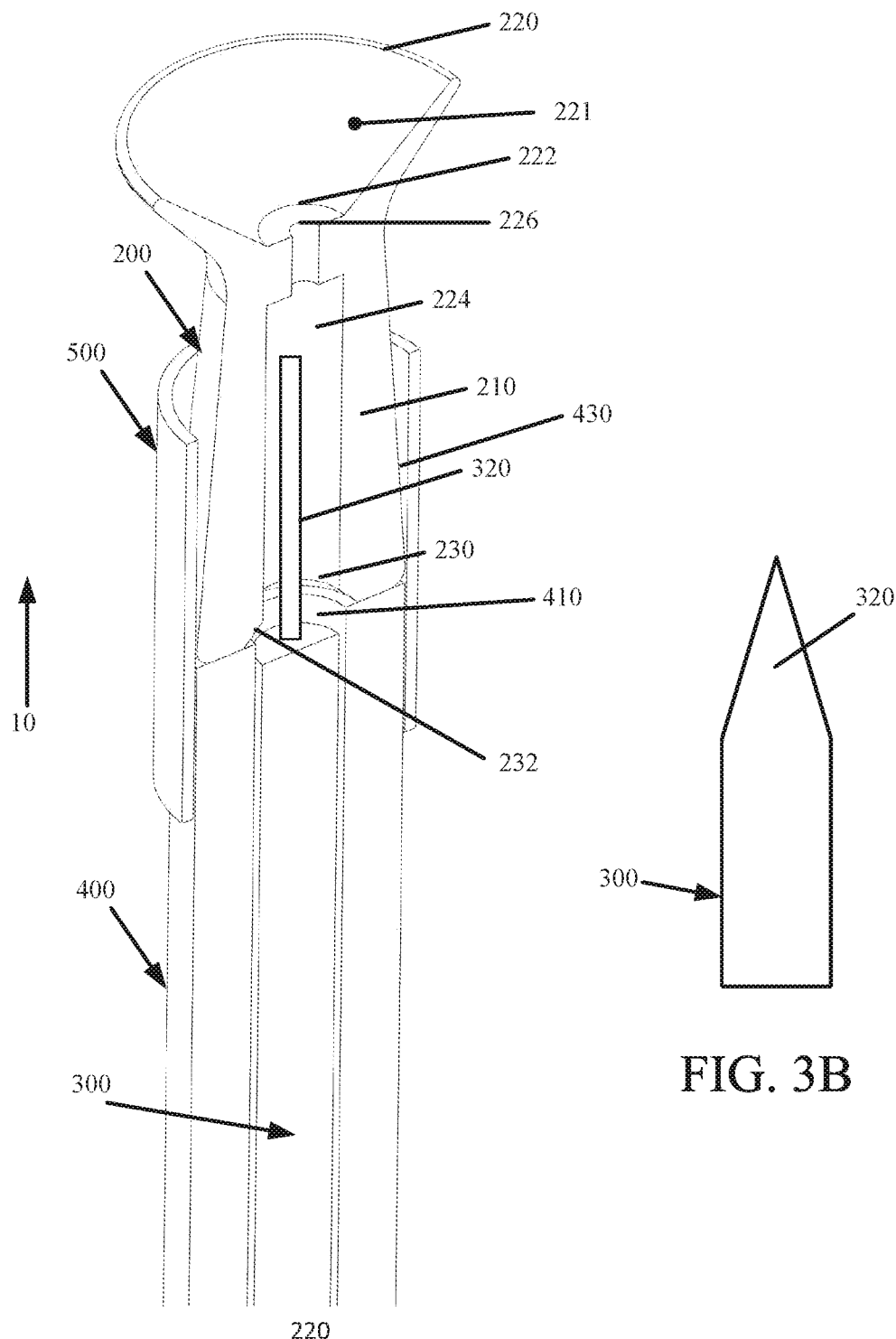
FIG. 3A is an enlarged cut-away view, taken along line 2-2' of the distal end of an embodiment of a lens manipulator, according to the subject invention. In this view, the lens manipulator is shown seated in the friction sleeve and the adjustment rod is removed from the lumen. Also shown is an embodiment of an alignment tip.
FIG. 3B shows an alternative embodiment of an alignment tip on an adjustment rod.

In a further embodiment, the tube portion has a lumen 224 that extends along the full longitudinal length 50 of the over-sleeve. At the proximal end 10, the lumen terminates within the concavity 221 of the suction cup. At the distal end 20, the lumen terminates in a rod opening 230 into which the proximal end 10 of the adjustment rod 300 can be inserted. In a further embodiment, the proximal end of the lumen narrows to form the pore 226, so that the diameter of the pore is less than the diameter of the lumen. An example of this is shown in FIGS. 2 and 3A.

The suction force generated by a suction cup is caused by the difference in air pressure between the outside and inside of the cup and the surface area of the object covered by the concavity 221 of the suction cup, If either one of these factors is increased or decreased, it can affect the amount of suction force produced by the suction cup. In one embodiment, the lumen 224 can he used to adjust the difference in air pressure between the outside and the inside of the suction cup. By moving the adjustment rod into or out of the lumen, the air pressure that can be generated under the suction cup can be altered. Ideally, the adjustment rod can be used to set or calibrate the amount of suction force that can be formed to meet individual needs and preferences.

In one embodiment, the diameter of the lumen is such that the adjustment rod is friction fit into the lumen, but can be adjusted into and out of the lumen to change the volume of the lumen. In a further embodiment, the adjustment rod and the lumen form an airtight seal between them, so that ambient air is inhibited from entering the lumen from the rod opening 230. Moving the rod into and out of the lumen to change the volume between the suction cup and the adjustment rod thereby changes or alters the amount of suction force that can be formed by the suction cup against a contact lens. In one embodiment, the amount of suction force generated by a suction cup is between approximately 100 grams/mm$^2$ and 150 grams. In further embodiment, the suction force generated by a suction cup of the subject invention is between approximately 110 grams and approximately 140 grams. In a specific embodiment, the suction force generated by a suction cup of the subject invention is approximately 130 grams.

The dimensions of an adjustment rod and lumen can depend upon the type of contact lens it will be used with, the amount of force necessary to hold a contact lens for insertion and removal, the dimensions of the suction cup, and other factors understood by those with skill in the art. In one embodiment, the lumen 224 has a longitudinal length 50 of between approximately 5 mm and approximately 20 mm. In more specific embodiment, the lumen has a longitudinal length of between approximately 10 mm and approximately 15 mm. In another embodiment, the adjustment rod 300 has a length of between approximately 5 mm and approximately 15 mm. In a more particular embodiment, the adjustment rod has a length of between approximately 8 mm and approximately 13 mm. In a specific embodiment, the adjustment rod has a length of about 10 mm.

A contact lens can form a strong adherence to the surface of the eye. This can be beneficial when wearing the contact lens. When removing the contact lens, such strong adherence can inhibit the removal of the contact lens. Unfortunately, it is not always possible to know in advance if a contact lens has formed a particularly strong adherence to the eye. When the suction cup 220 is placed against the contact lens on an eye, the suction cup can be pushed against the contact lens to form the suction force, by forcing air out of the concavity 221 under the suction cup. Once this suction force is generated, it can be difficult to remove the suction cup from the contact lens without applying a significant, and potentially harmful, amount of pull force against the suction cup, which can be transmitted to the surface of the eye.

Embodiments of the subject invention provide an advantageous safety mechanism by which the suction cup can be removed without application of an excessive amount of pull force against the contact lens. In one embodiment, a friction fit between the adjustment rod 300 and the lumen 224 is configured to cause the adjustment rod to be removed from the lumen if a pre-determined amount of pull force is applied to the lens manipulator. When the adjustment rod is pulled from the lumen, the lumen volume fills with ambient air, thereby equilibrating the external pressure and the internal pressure of the suction cup. This eliminates the suction force on the contact lens, so that the now stand-alone over-sleeve can be manually removed or may self-release from the contact lens. In one embodiment, the diameter of the adjustment rod is at least 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm, 3.2 mm, 3.3 mm, 3.4 mm, and 3.5 mm, or a diameter that is a range between any two of the listed values.

Once the over-sleeve has been removed, the rod can be reinserted into the rod opening to, again, be used to adjust the volume of the lumen. In one embodiment, the distal end of the rod opening 230 has a bevel or chamfer 232 around it to aid in insertion of the adjustment rod. FIGS. 2 and 3A illustrate an example of a rod opening with a chamfered edge.

Figure 4:
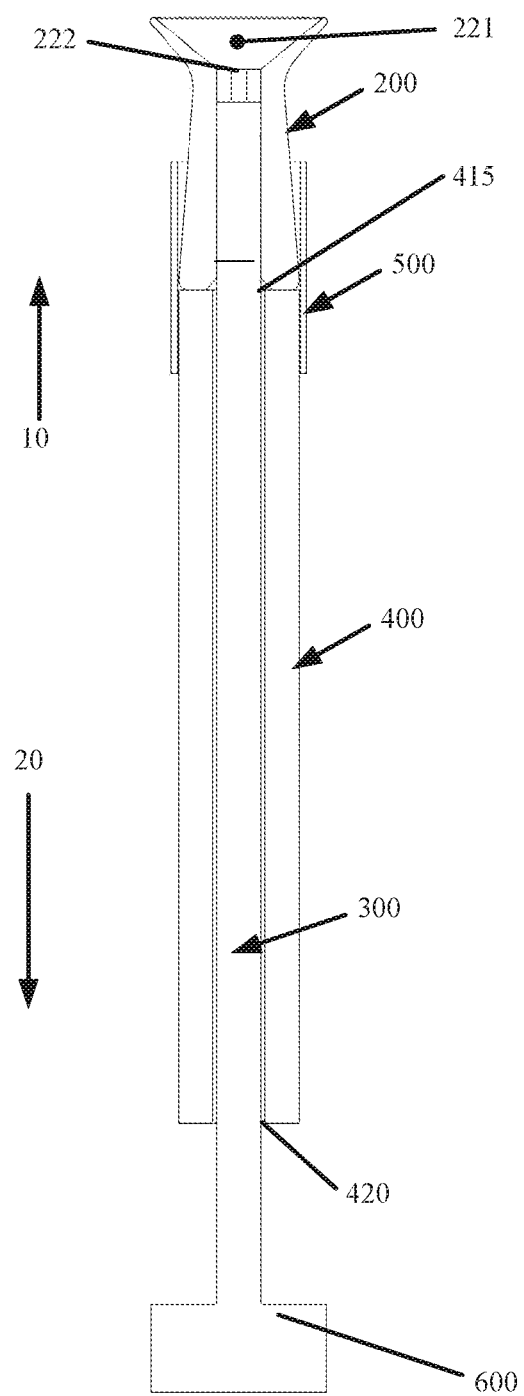
FIG. 4 shows a front elevation view of an embodiment of a lens manipulator.

As mentioned above, the ability to remove the adjustment rod 300 from the lumen 224 can provide an advantageous safety mechanism for releasing the suction force in the suction cup, thereby preventing undesirable or excessive pulling force on the eye and/or contact lens thereon. In order to ensure quick release of the suction force, the adjustment rod can be inserted into the lumen a sufficient distance to block the lumen and allow the suction force to be formed, but not so great a distance that it cannot be quickly removed to release the suction. FIG. 4 illustrates an example of an adjustment rod inserted into the lumen a sufficient distance to allow suction to be formed and still be quickly removed from the lumen.

Depending upon the dimensions and configuration of the over-sleeve, the adjustment rod may not fill more than a small portion of the volume of the lumen 224. The remaining open space of the lumen can cause more suction force than necessary to be formed under the suction cup. In one embodiment, the proximal end 10 of the adjustment rod can be configured with a spacer 320 to reduce the volume of the lumen, without increasing the friction force by having to insert the rod further into the lumen. A spacer can be a narrower extension from the proximal end 10 of the adjustment rod. FIG. 3A illustrates one example of a spacer that is rod, narrower than the adjustment rod, which juts from the proximal end of the adjustment rod. FIG. 3B illustrates another example of a spacer that is a conical extension at the proximal end of the adjustment rod. The use of a spacer on an adjustment rod allows the rod to be inserted only as far as necessary to block air flow and the remaining volume to be reduced to control the suction force of the suction cup. In one embodiment, the spacer 320 does not make contact with the lumen. In an alternative embodiment, the spacer can make at least some contact with the lumen, thereby providing another area of friction that can inhibit the over-sleeve being removed from the adjustment rod.

A further advantage of a spacer is that is permits a user to pull the adjustment rod out of the lumen far enough to allow the ingress of ambient air into the lumen, leaving the spacer in the lumen. This allows replacement of the adjustment rod in the lumen more easily and, if necessary, without seeing the rod opening, since the spacer can align the adjustment rod and lumen. The above-mentioned chamfered or beveled edge 232 around the rod opening 230 can also facilitate reinsertion of the spacer and adjustment rod.

The dimensions of a spacer can vary, depending upon the longitudinal length of the lumen, the length of the adjustment rod, and how much of the adjustment rod is inserted into the lumen. In one embodiment, the dimensions of a spacer are such that, when the adjustment rod is positioned within the lumen, the spacer reduces the remaining volume in the lumen by between approximately 25% and approximately 85%. In a further embodiment, the dimensions of a spacer are such that, when the adjustment rod is positioned within the lumen, the spacer reduces the remaining volume in the lumen by between approximately 35% and approximately 75%. In a more specific embodiment, the dimensions of a spacer are such that, when the adjustment rod is positioned within the lumen, the spacer reduces the remaining volume in the lumen by between approximately 45% and approximately 65%. In a specific embodiment, when the adjustment rod is positioned within the lumen, the spacer reduces the remaining volume in the lumen by approximately 50%.

The overall length of an over-sleeve can depend upon the required length of the lumen, the dimensions of the suction cup, the length of the tube portion, and other factors known to those having skill in the art. In one embodiment, the overall length of an over-sleeve is between approximately 20 mm and approximately 40 mm. In a further embodiment, the overall length of an over-sleeve is between approximately 23 mm and approximately 37 mm. In a specific embodiment, the overall length of an over-sleeve is approximately 25 mm.

Once it has been determined how much of the length of the adjustment rod 300 should extend into the lumen, to provide the desired suction force, it can be beneficial for that specific length to be set or fixed for the lens manipulator during use. In one embodiment, there can be visual indicators 330 on the rod that can be used to determine how much of the adjustment rod extends into the lumen. For example, graduated marks on the adjustment rod can be used to check the amount of adjustment rod in the lumen. FIG. 2 illustrates a non-limiting example of visual indicators. A friction fit between the adjustment rod and lumen can aid in maintaining the length where indicated.

FIGS. 2 and 4 illustrate embodiments having the adjustment rod and over-sleeve collinear with the longitudinal length 50 of the lens manipulator 100. These embodiments allow the lens manipulator to be held substantially vertical or perpendicular to the ground, with the lens cup directed upwards for use. In use, the lens manipulator can be held in one hand in front of the body. By bending forward, towards the hand holding the lens manipulator, the eye can be brought into proximity with the suction cup to install or remove a contact lens on the eye.

In a further embodiment, a tensioning sleeve 400 can be used on the adjustment rod 300. In one embodiment, the tensioning sleeve is generally tubular structure that has a bore 410. In one embodiment, the bore opens onto and forms an aperture 415 at the proximal end 10. There can also be an exit 420 on the distal end 20. The adjustment rod can be frictionally fit into the tensioning sleeve. By moving the adjustment rod into and out of the aperture, the length of the adjustment rod that extends into the lumen can be adjusted. When the over-sleeve is positioned on the proximal end of the adjustment rod, the distal end of the over-sleeve can abut against the proximal end of the tensioning sleeve. Thus, only the length of adjustment rod that extends from the aperture will extend into the lumen of the over-sleeve. FIG. 2 illustrates a non-limiting example of a tensioning sleeve with an adjustment rod extending from the aperture. FIGS. 3A and 4 illustrate non-limiting examples of the over-sleeve sitting on an adjustment rod and abutting the proximal end of the tensioning sleeve.

The frictional fit of the over-sleeve 200 on the adjustment rod 300 can determine the maximum amount of force necessary to pull the rod from the lumen 224. The ability to remove the adjustment rod from the lumen provides an advantageous safety release to prevent excessive and undesirable pulling force being applied to the eye. As discussed above, in one embodiment the rod and the lumen form a friction fit that releases upon application of a pre-determined amount of pull force.

Figure 5A:
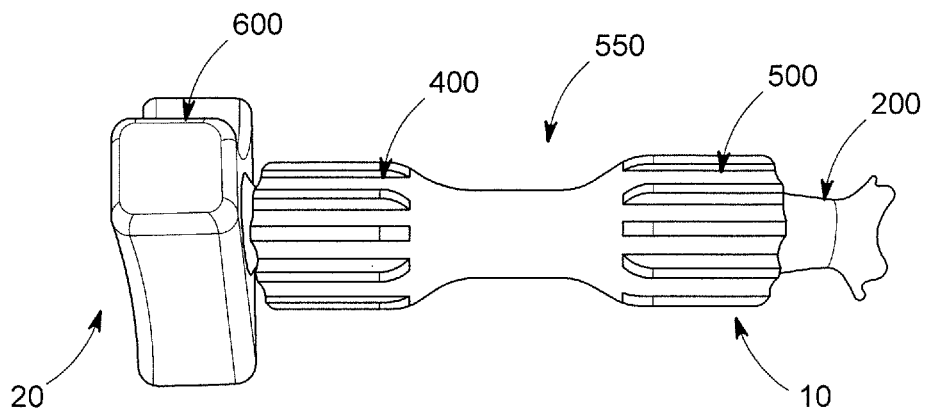
FIGS. 5A, 5B, and 5C are a photograph of an embodiment of a lens manipulator in different stages of assembly.
Figure 6:
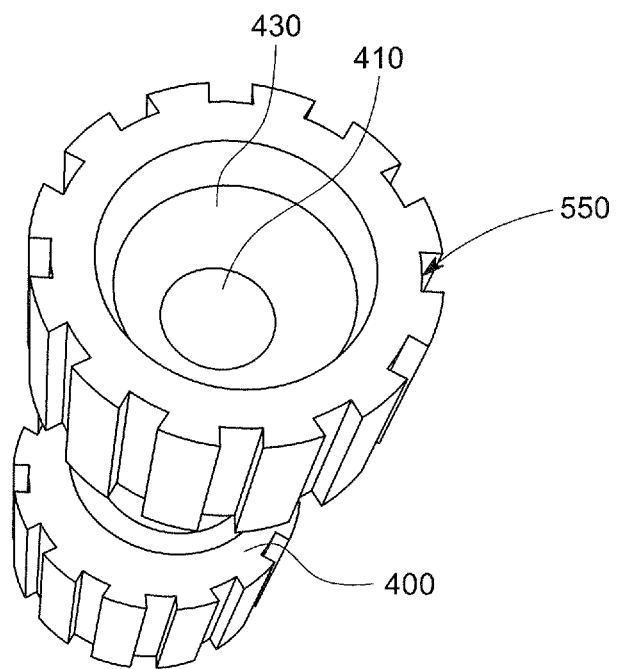
FIG. 6 is a photograph of an embodiment of an over-sleeve.

In another embodiment, a cuff 500 can be used to provide a frictional fit with the over-sleeve. A cuff can be a tubular shape, as shown, for example, in FIGS. 1 and 2, that surrounds a proximal portion of the tensioning sleeve 400 to form a seat 430 around the over-sleeve. In one embodiment, the cuff makes at least partial contact with the over-sleeve when positioned in the seat, such as shown, for example, in FIGS. 3A and 4. The cuff can provide resistance to the over-sleeve being lifted off of the adjustment rod. The seat formed by the cuff can also act as a guide for reattaching or reseating the over-sleeve on the adjustment rod. FIG. 5A and 6 illustrate an alternative embodiment of a cuff integrated with or formed as part of the tensioning sleeve. Embodiments of a lens manipulator having an over-sleeve and adjustment rod that are collinear with the longitude of the lens manipulator, such as shown, for example in FIGS. 1, 2, 3A, 4, 5A, and 6, can include a cuff that is collinear with the longitude, as shown in FIGS. 2 and 4.

As discussed above, when the contact lens forms too strong an adherence to the eye, it can be difficult to remove the contact with the suction cup 220. If the suction cup is placed on a too-strongly adhering contact, the adjustment rod can be withdrawn from the lumen 224, which allows air into the lumen to counter-act the suction under the suction cup. In a further embodiment, the cuff can act as a safety mechanism by which the over-sleeve can be forcibly removed from the adjustment rod 300. If the adjustment rod needs to be removed from the lumen, the cuff 500 can be slid towards the over-sleeve until the seat 430 in the cuff pushes the over-sleeve off the adjustment rod.

In yet another embodiment, the adjustment rod 300 can have a detent 340 at or at about the proximal end 10. The detent can engage with the lumen in the over-sleeve 200. A detent can provide a frictional fit or resistance that inhibits the over-sleeve from being removed from the adjustable rod until or unless a pre-determined amount of pull force is applied to the over-sleeve. In a further embodiment, the lumen can be configured with a length that provides the necessary resistance under normal use and allows the over-sleeve to come off of the adjustment rod if an excessive pull force is applied to the suction cup. A detent can be any of a variety of surface features or apparatuses that push against or otherwise engage with the wall of the lumen. For example, a detent can be a barb, raised rib, or shoulder that protrudes radially from the adjustment rod, such as shown in FIGS. 5C, 15-18, 19, and 22. By way of another example, a detent can be a spring-loaded ball that retracts into the adjustment rod. Spring-loaded balls used for frictionally engaging two objects are well-known in the art and, thus, have not been shown.

Specific frictional forces and/or resistance forces are necessary to maintain the over-sleeve on the adjustment rod during normal use and provide a safety release that allows the over-sleeve to be disengaged from the adjustment rod under certain conditions. The embodiments disclosed herein provide several devices and techniques for configuring and adjusting one or more these forces. These techniques and devices can be used singularly or in combination.

Figure 5B:
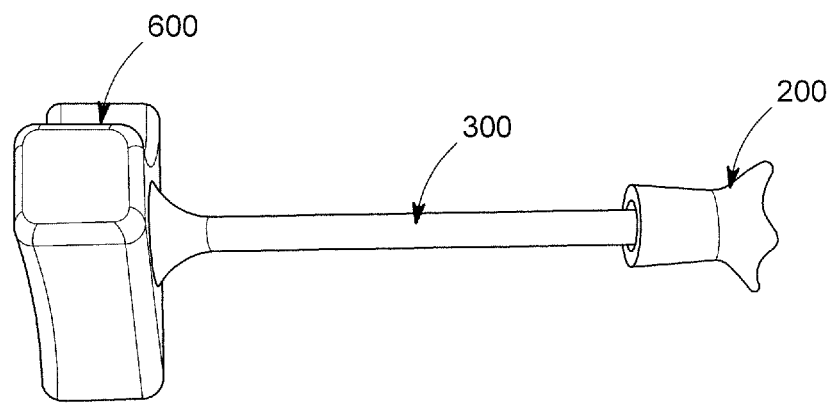
Figure 5C:
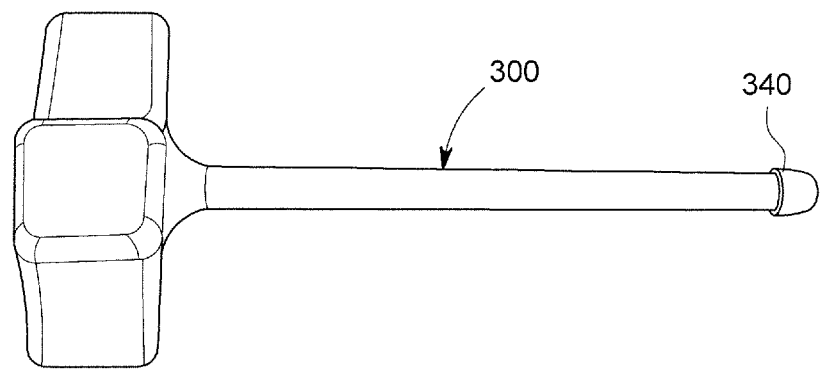

FIGS. 5A, 5B and 5C illustrate an embodiment that utilizes all of the devices and techniques described above. FIG. 5A shows an embodiment of a fully assembled lens manipulator that has sliding-sleeve 550 that is a tensioning sleeve 400 integrated with a cuff 500 formed at the end of the tensioning sleeve. FIG. 6 illustrates a sliding-sleeve and the seat 430 in the cuff end. FIG. 5A shows an over-sleeve disposed within the seat 430 in the cuff end. FIG. 5B is a partially disassembled view that shows the adjustment rod 300 with the over-sleeve on the proximal end 10. FIG. 5C shows the adjustment rod with a detent 340 at the proximal end that can be used to provide resistance to hold the over-sleeve on the proximal end. With this embodiment, the lumen of the over-sleeve can be configured with a length and diameter that provides sufficient suction force and resistance during normal use, but also provides a safety release that operates when excessive pull force is applied to the suction cup. Alternatively, the sliding-sleeve can be used to manually remove the over-sleeve from the adjustment rod. The sliding-sleeve 550 can be pushed or slid towards the proximal end 10 of the adjustment rod 300, thereby causing the over-sleeve to be pushed off the adjustment rod. Other embodiments can use various combinations of a cuff, adjustment rod, and lumen in the over-sleeve, and a detent to achieve the desired frictional and resistance forces.

Figure 7:
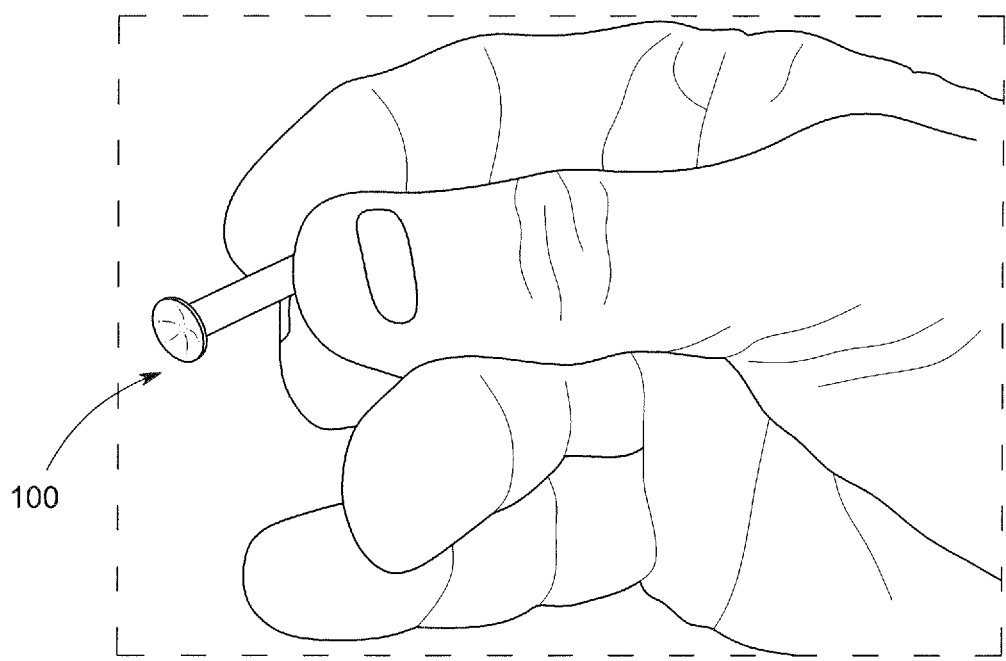
FIG. 7 is a photograph of a lens manipulator held in a hand to show how it is manipulated.
Figure 8:
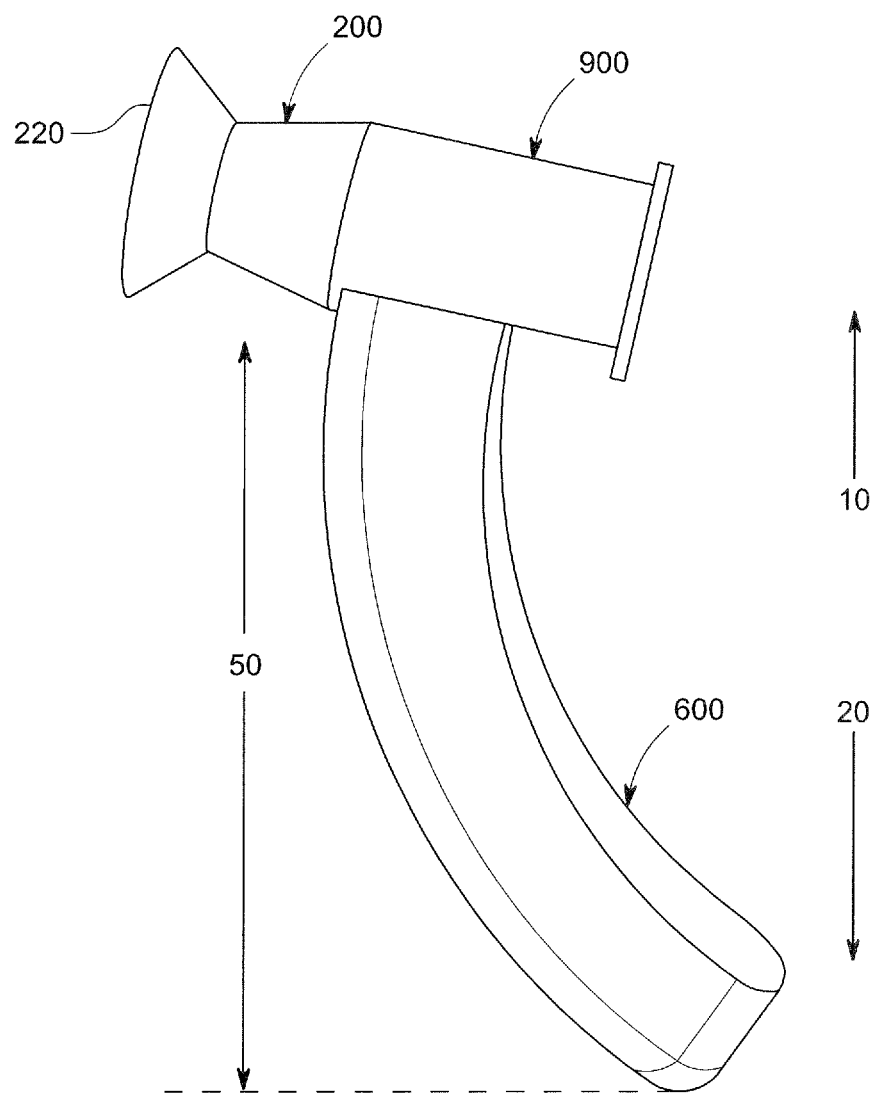
FIGS. 8, 9, and 10 are images of another alternative embodiment of a lens manipulator, wherein the proximal end of the adjustment rod, the over-sleeve, and finger slide are turned approximately 90° relative to the longitudinal length of the lens manipulator.
Figure 9:
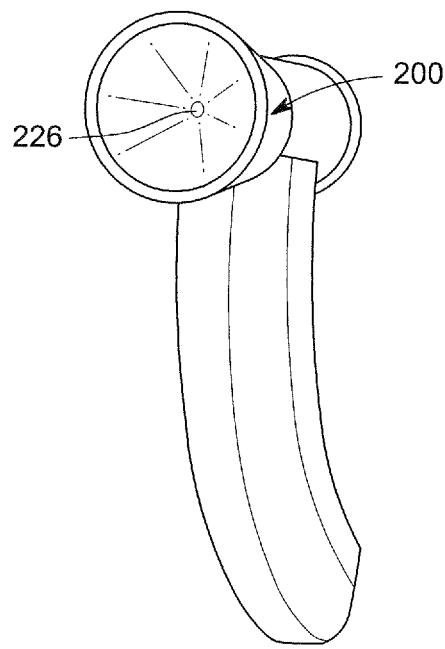
Figure 10:
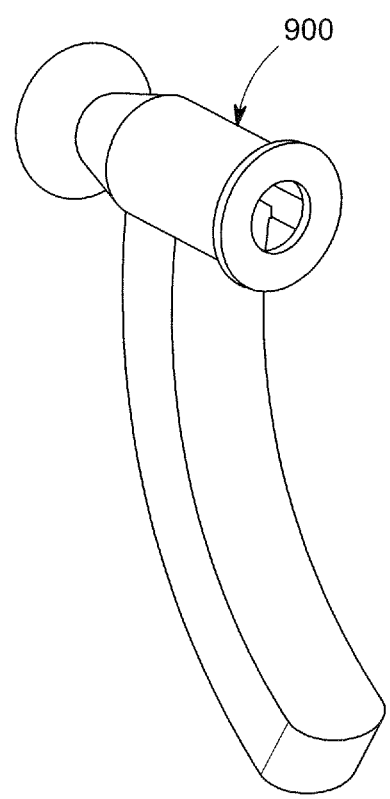
Figure 11:
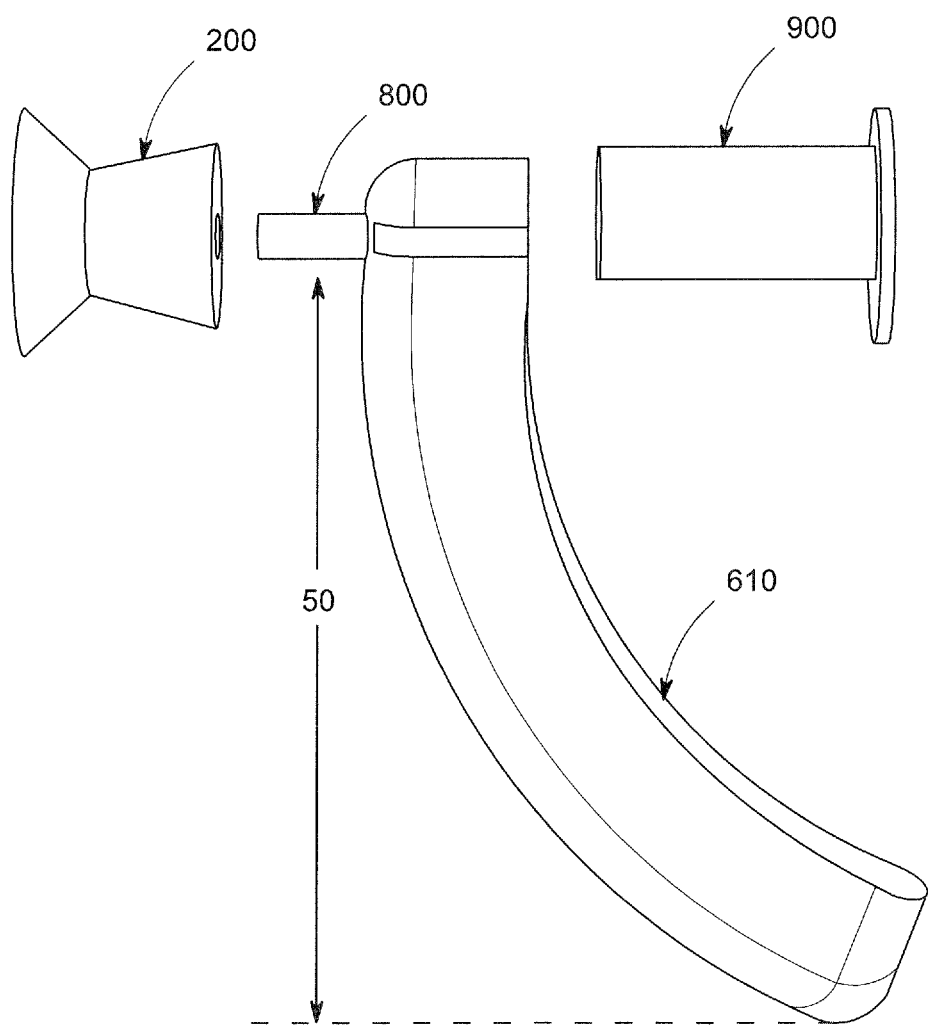
FIGS. 11, 12, 13, and 14 are images of the alternative embodiment in FIGS. 8, 9, and 10, shown in exploded views.
Figure 12:
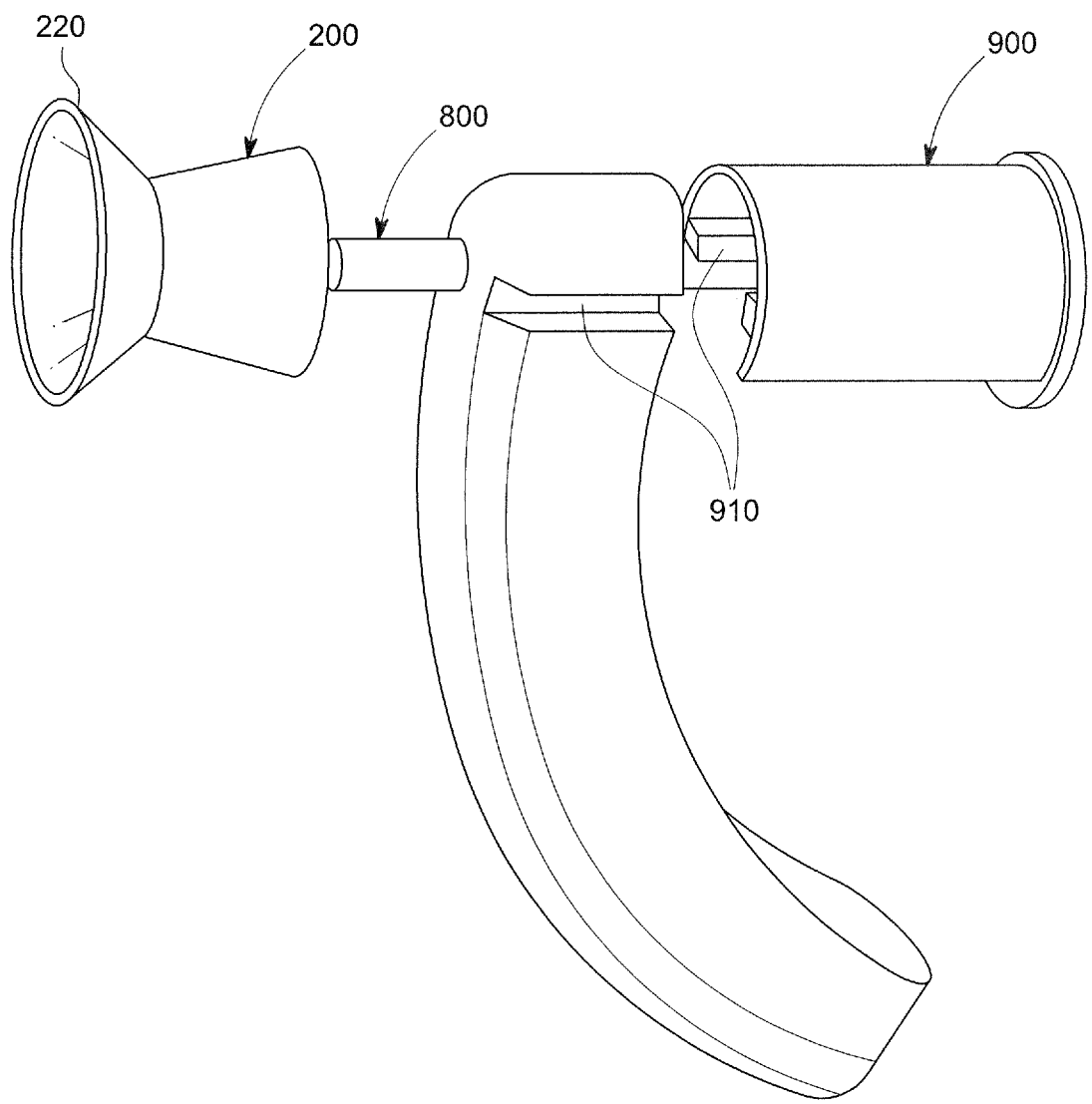
Figure 13:
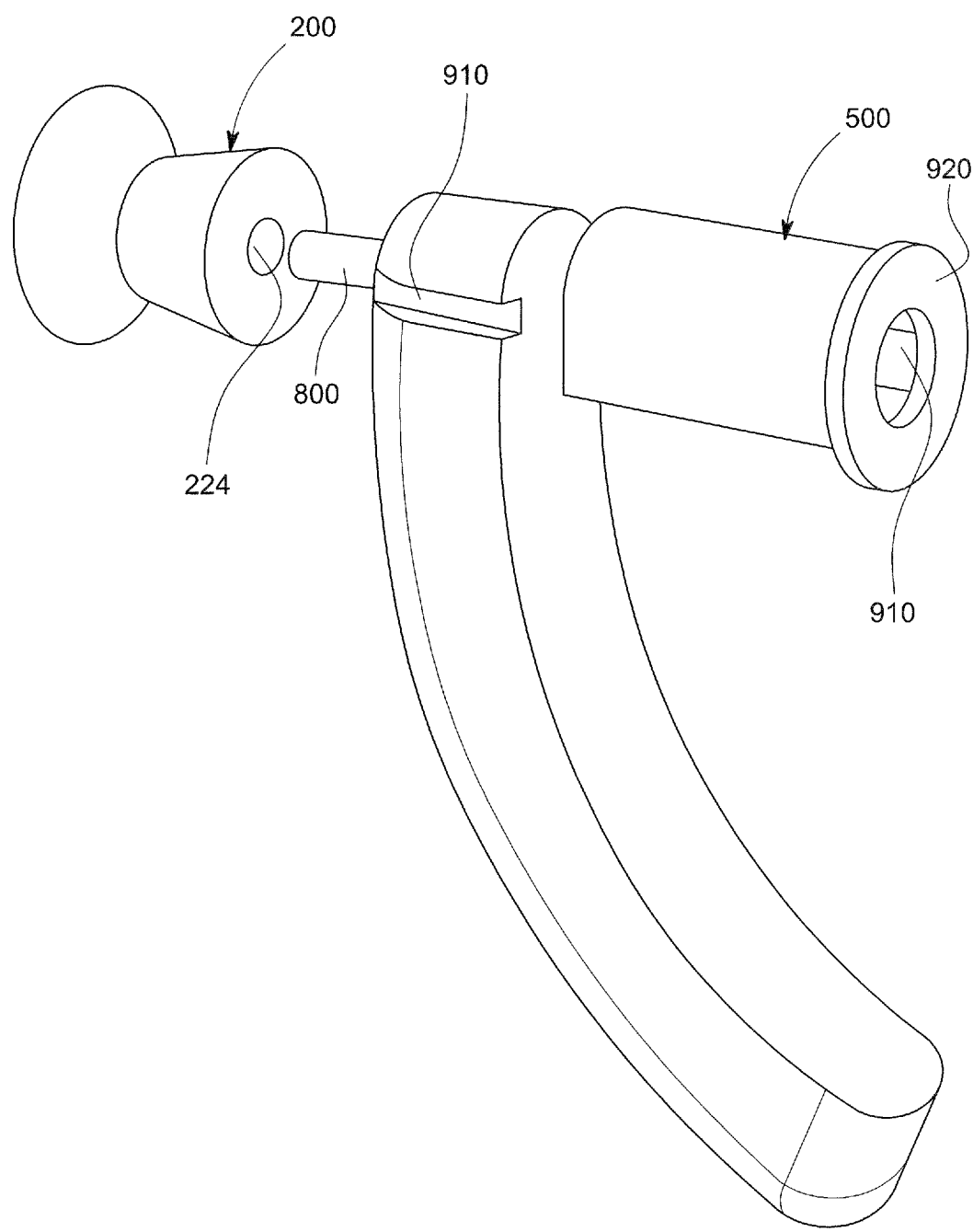
Figure 14:
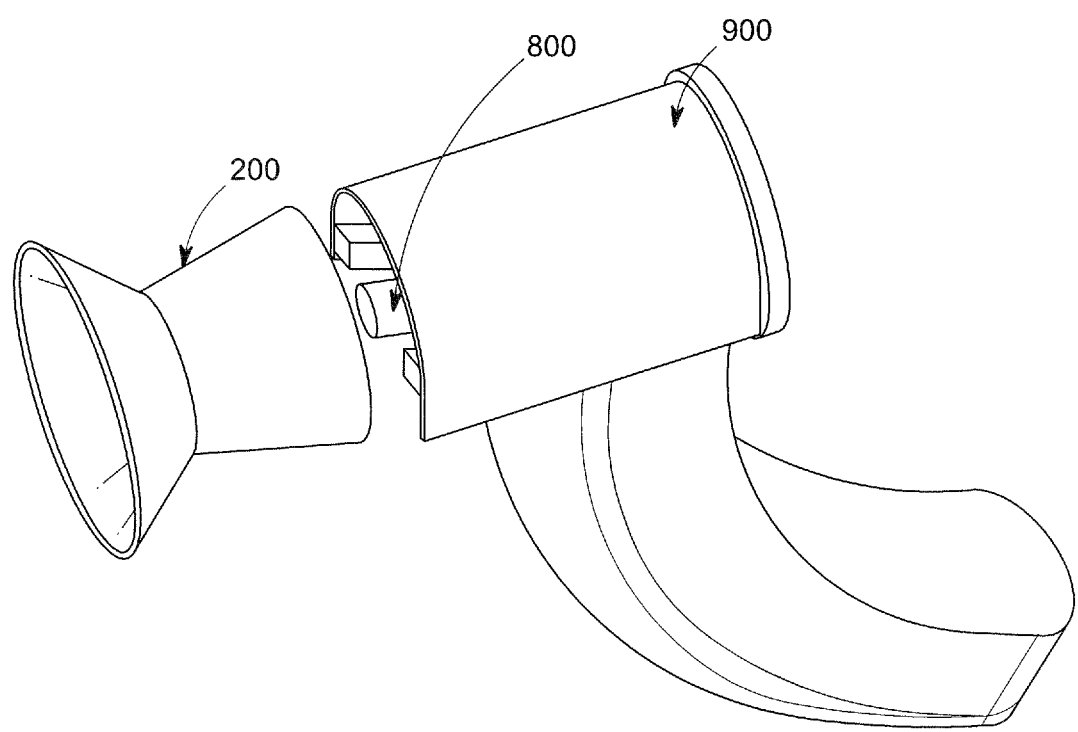
Figure 15:
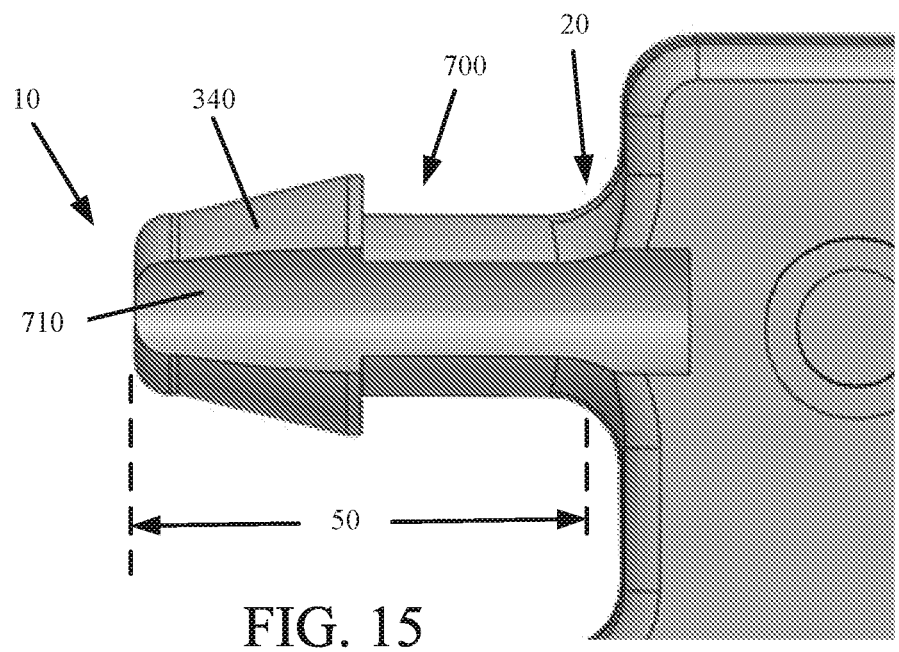
FIGS. 15, 16, 17, and 18 illustrate one embodiment of an insertion stem, according to the subject invention.

The embodiments of the subject invention can be used manually. FIG. 7 illustrates how the fingers and palm can be used to hold and control the lens manipulator. In one embodiment, the fingers on one hand can be used to remove the over-sleeve from the adjustment rod, should the safety release not be sufficient. There can be various ergonomic structures 600 on the lens manipulator to assist with holding and manipulating the over-sleeve. FIGS. 5A, 5B, and 5C illustrate an ergonomic structure in the form of an enlarged handle 610 at the distal end 20 of an adjustment rod that can be held in the palm. FIG. 6 illustrates ribbing on the external surface of the cuff and the tensioning sleeve that can assist with holding the lens manipulator. FIG. 7 illustrates a lens manipulator made of a material that forms stiction with fingers. FIGS. 8, 9, and 10 illustrate examples of a handle having an ergonomic curvature that aids in holding and manipulating the position of the over-sleeve and suction cup. It can be advantageous if the ergonomic structures 600 allow the lens manipulator to be held in, or on, one hand or one or more fingers of one hand. It can be further advantageous if the ergonomic structures allow the lens manipulator to be held such that at least one, preferably two, fingers of the holding hand are free to move the eyelid(s) away from the eye during use of the lens manipulator. For example, ergonomic structures or design can allow the lens manipulator to be held with the thumb and forefinger, thus leaving at least the second and third fingers free to extend forward and move the lower eyelid downward, while the suction cup simultaneously advances towards the eye. Other ergonomic structures that provide the same or similar benefits are within the scope of the subject invention.

In an alternative embodiment, the adjustment rod 300 is replaced with a stem 310 that is bent, turned, or otherwise angled, relative to the longitudinal length 50 of the lens manipulator. In a further embodiment, an over-sleeve 200, when operably connected to the angled or bent stem will also be non-collinear with the longitude 50 of the lens manipulator. FIGS. 11, 12, 13, 15, 19, 23, and 24 illustrate non-limiting examples of a stem. The stem can have a fixed length and position, such that the over-sleeve operably connects to the stem, through the rod opening 230, without the need for adjustment. Thus, the stem will insert into the lumen 224 of the over-sleeve the same, or substantially the same, distance each time the over-sleeve is placed thereon. The stem can perform the same function as an adjustment rod 300 in blocking the lumen to inhibit ingress of air from the rod opening.

In one embodiment, the lens manipulator has ergonomic structures 600, for example, a handle 610, which facilitates holding and manipulating the over-sleeve 200. With embodiments having a stem, the ergonomic structures are held so that the ergonomic structures of the lens manipulator are at least partially out of the direct line of sight when the suction cup is directed towards the eye for use. More specifically, the lens manipulator can have a handle that allows the lens manipulator to be held with the hand(s) out of the direct line of sight when the eye approaches the suction cup of the over-sleeve. FIGS. 8-14 and 19-23 illustrate non-limiting examples of a lens manipulator with a stem bent or angled or otherwise non-collinear relative to the longitudinal length 50 and a handle that allows the lens manipulator to be held without the hand being in the direct line of sight of the suction cup. This arrangement can be ergonomically advantageous and can inhibit interference by the hand or ergonomic structures with viewing the suction cup as the eye approaches the over-sleeve. It can also allow one or more fingers on the same hand that holds the lens manipulator to be used for moving an eyelid away from the eye while simultaneously advancing the contact lens towards the eye.

In one embodiment, the stem has an angle of between approximately 60° and approximately 120°, relative to the longitudinal length or the distal end of the adjustment rod. In a more particular embodiment, the stem has an angle of between approximately 70° and approximately 110° relative to the longitudinal length or the distal end of the adjustment rod. In specific embodiment, the stem has an angle of between approximately 80° and approximately 100° relative to the longitudinal length or the distal end of the adjustment rod. In a more specific embodiment, the stem has an angle of approximately 90° relative to the longitudinal length or the distal end of the adjustment rod. One non-limiting example of this more specific embodiment is shown, for example, in FIGS. 11 and 12.

The above-described embodiments pertain to a lens manipulator having a single adjustment rod or stem. With these embodiments, an over-sleeve 200 is used with the single adjustment rod for both insertion and extraction of a contact lens. This arrangement is convenient, easy to use, compact, and allows individual adjustment and calibration of the maximum pulling force. The ability to calibrate the adjustment rod can be advantageous for certain types of contact lens, where automatic removal of the over-sleeve, via the safety feature, is preferred, and other situations where it can be beneficial to control the maximum suction force applied to a contact lens and/or eye.

Figure 22A:
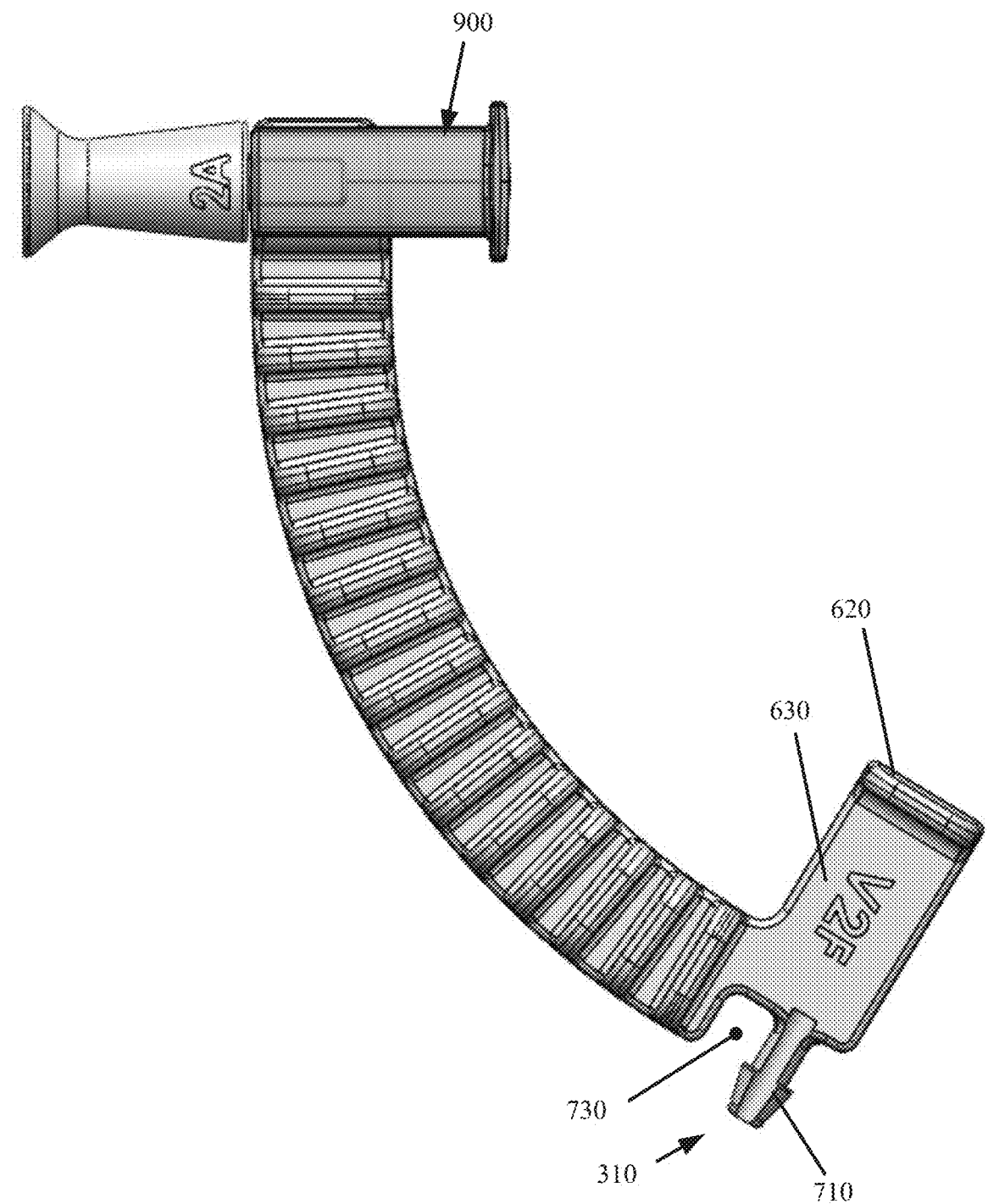
FIGS. 22A and 22B illustrate embodiments of a lens manipulator having an insertion stem and an extraction stem configured with a finger-slide to remove an over-sleeve from the extraction stem.
Figure 22B:
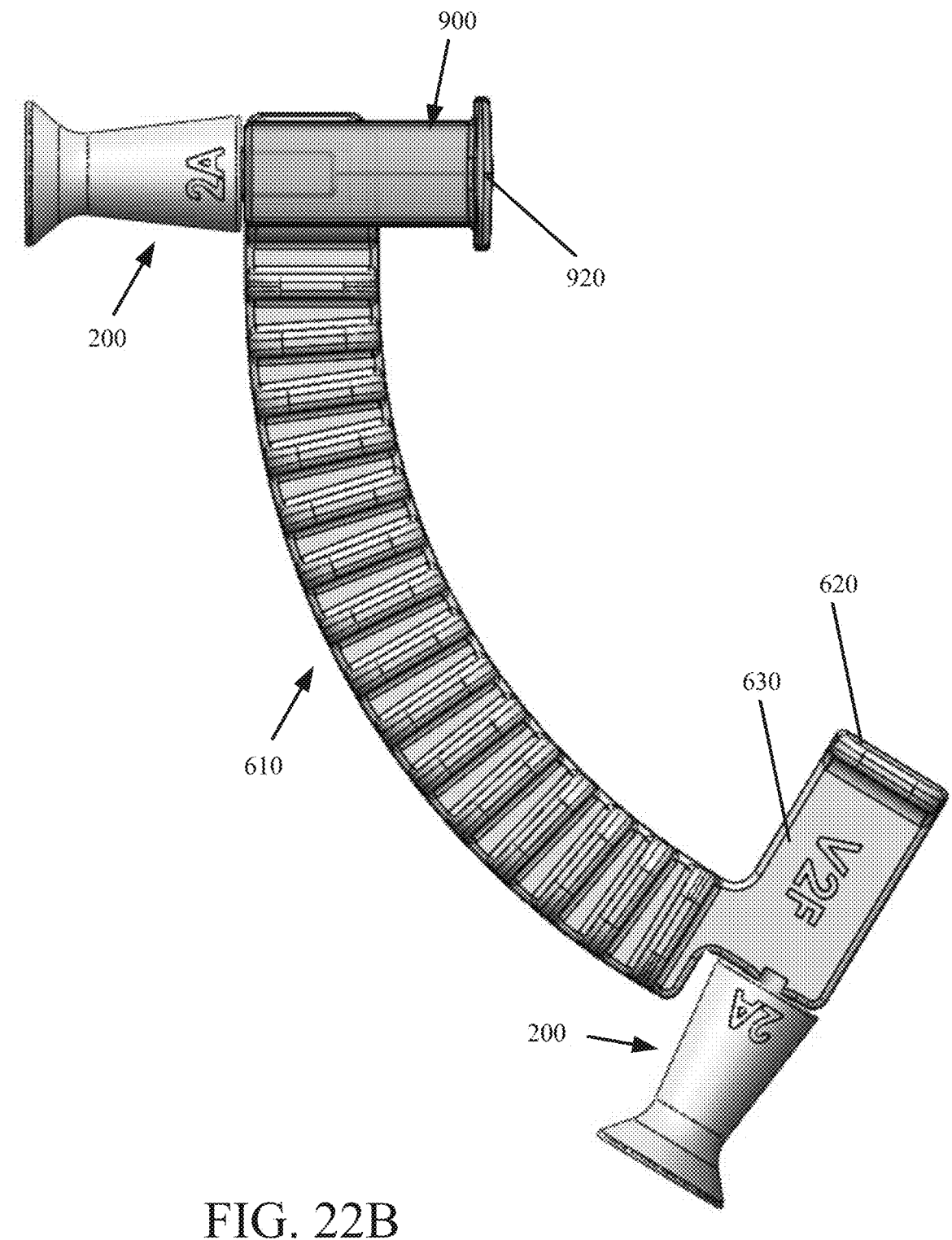
Figure 23:
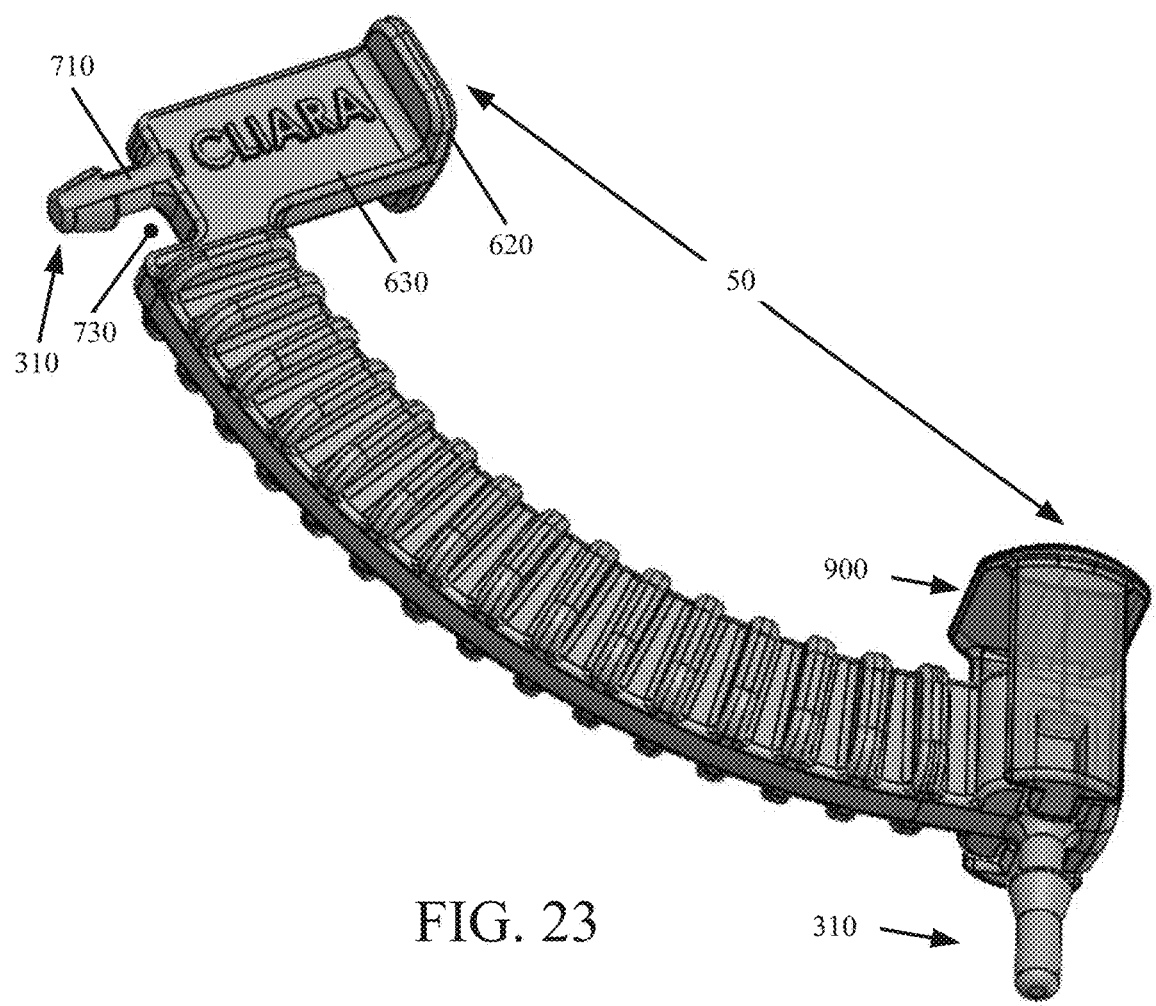
FIG. 23 illustrates an embodiment of a lens manipulator having an insertion stem at one end of a handle and an extraction stem configured with a finger-slide to remove an over-sleeve from the extraction stem on another end of a handle.
Figure 24:
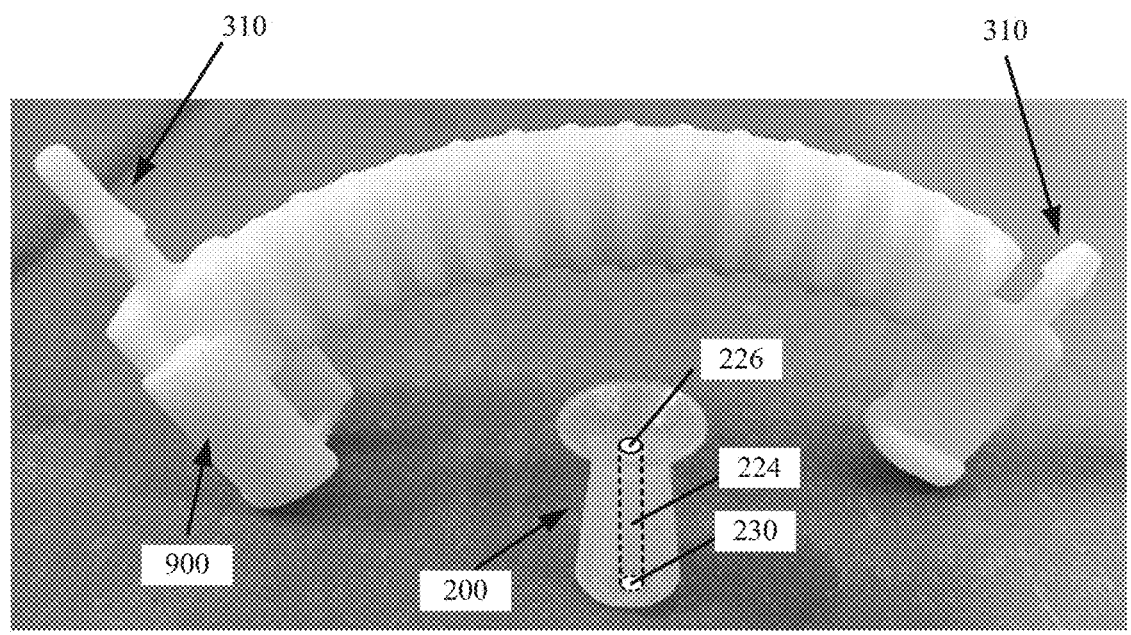
FIG. 24 illustrates an embodiment of a lens manipulator having an insertion stem and an extraction stem configured with a finger-slide. Also shown is an embodiment of an over-sleeve that can be used with both the extraction stem and insertion stem.

An alternative embodiment employs a lens manipulator with a dual-stem configuration, as shown, for example, in FIGS. 22-24. With this embodiment, an over-sleeve 200 can be operably connected to each stem. Alternatively, one over-sleeve can be configured for use on both stems and operably connected on whichever stem is required. The dual-stem lens manipulator embodiment can have both an insertion stem 700 and an extraction stem 800.

In a further embodiment, the dual-stem configuration is arranged on an ergonomic structure 600, such as, for example, a handle 610, by which the dual-stems can be manipulated for use. The dual stems can be arranged in any of a variety of locations or positions on the ergonomic structure, including, but not limited to, side by side, opposite sides facing different directions, at each end facing the same direction, at opposite ends facing different directions, or other arrangements. FIGS. 22-24 illustrate a specific embodiment having an ergonomic structure 600 which is an elongated handle 610 on which the dual-stems are arranged at opposite ends of the elongated handle. Additional ergonomic structures can also be utilized, such as a finger rest 620, associated with the insertion stem 700 and a finger rest support 630. Embodiments employing a dual-stem configuration are not limited to any particular arrangement of the stems, as long as each can be utilized for the intended purposes of inserting and extracting contact lenses.

An insertion stem can be operably connected to an over-sleeve 200 which can support a contact lens while it is being inserted onto an eye. As discussed above, it is important that suction force be inhibited between a suction cup 220 of the over-sleeve and the contact lens, when the contact lens is being inserted. Such suction force can interfere with deposition of the contact lens onto the eye. One method for inhibiting formation of a suction force is to place the contact lens on the suction cup in a fashion that inhibits formation of a suction force. Alternatively, the insertion stem can be configured to inhibit the formation of suction force under the suction cup.

Figure 16:
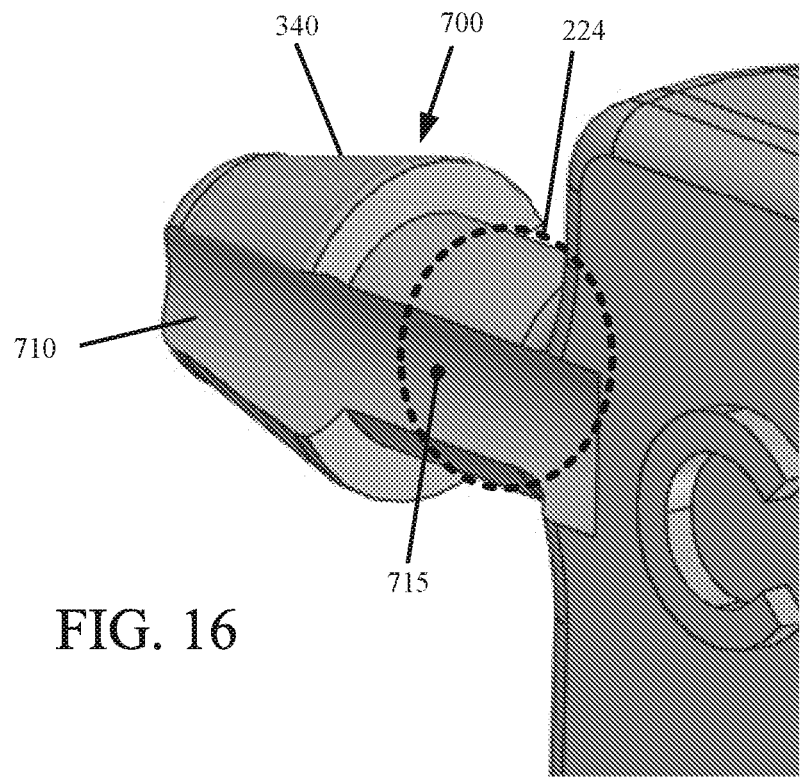
Figure 17:
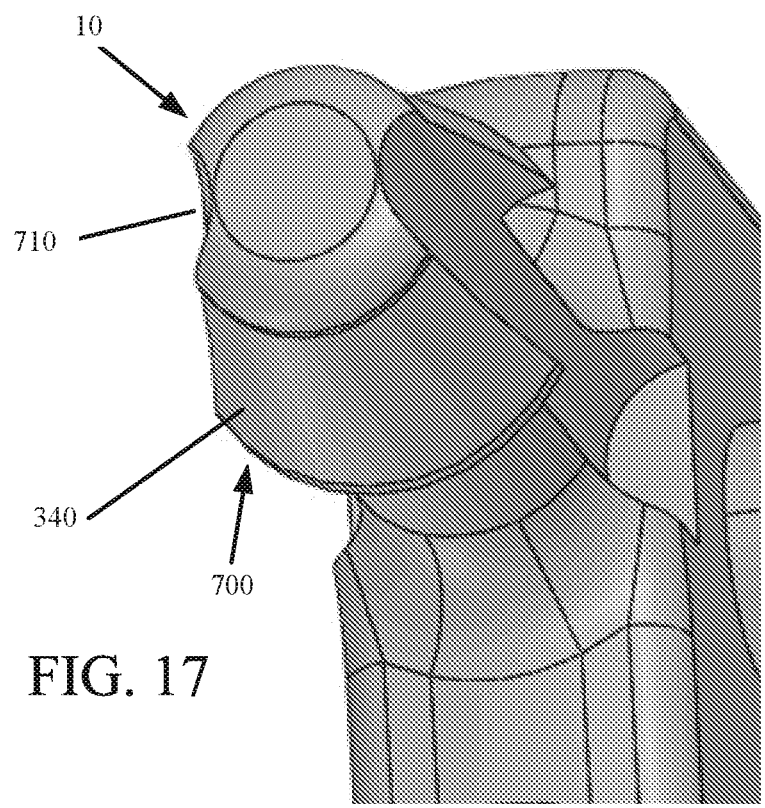
Figure 18:
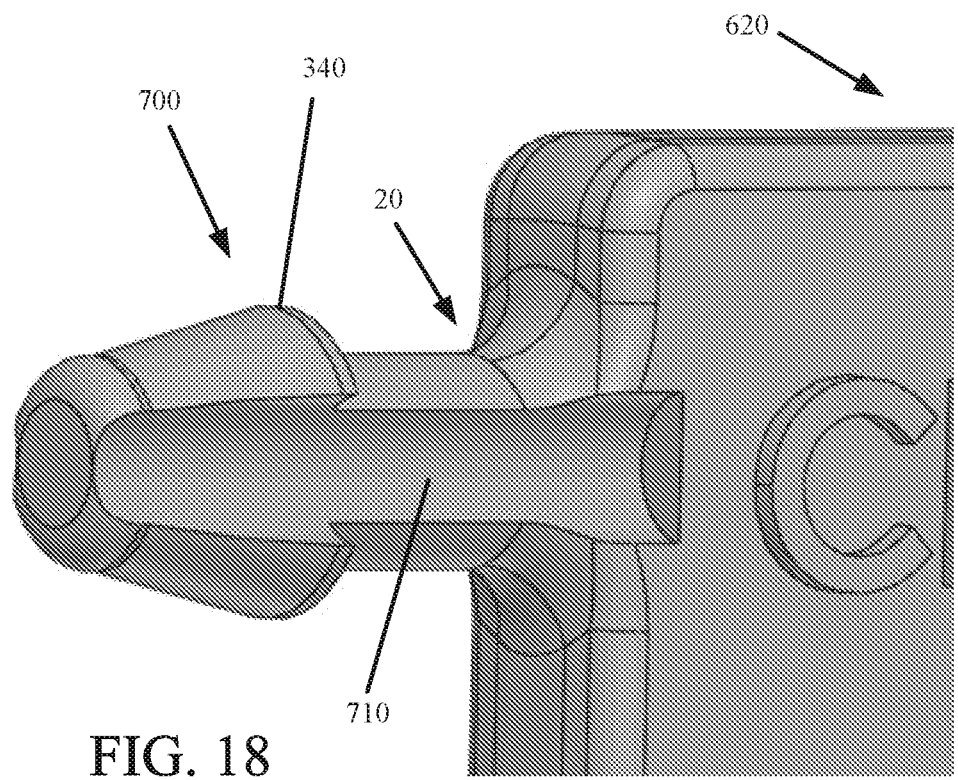

In one embodiment, the insertion stem 700 has at least one vent 710 that forms an indentation along the longitudinal length 50 between the proximal end 10 and the distal end 20 of the insertion stem 700. The vent allows air or other gases into the lumen 224 when an over-sleeve 200 is operably connected to the insertion stem. FIGS. 15-18 illustrate non-limiting examples of a vent on an insertion stem. When an over-sleeve is operably-connected to the stem, the indentation of the vent creates a space or channel 715 between the insertion stem and the lumen 224, as illustrated in FIG. 16, which allows air and other gases into the lumen and under the suction cup. The channel extends to and opens on the proximal end 10 of the insertion stem and extends in the distal direction past the point where the over-sleeve operably engages with the insertion stem. Thus, when the over-sleeve is operably connected to the insertion stem, the vent extends at least from the pore 226 and past the rod opening 230 of the lumen. This creates a channel along the full longitudinal length of the lumen. As discussed above, when air is allowed under the suction cup, a suction force is inhibited. Thus, the vent can inhibit a suction force between the suction cup and a contact lens placed thereon.

In a further embodiment, the insertion stem can include one or more detents 340, similar to those described above for use on an adjustment rod 300. In one embodiment, the detent is a barb, raised rib, or shoulder that extends radially from the insertion stem, an example of which is shown in FIGS. 15-18. In a further embodiment, a vent 710 can extend through the detent to form the channel 715 along the longitudinal length of the lumen 224 of the insertion stem 700.

When inserting a contact lens onto the eye, the eyelashes and eyelid are retracted, either by widely opening the eye or, more often, by using one or more fingers to retract one or both of the eyelids. To inhibit the hand holding the ergonomic structure that supports the insertion stem from contacting the face, eyelids, or other areas around the eye, the insertion stem can be configured to support the over-sleeve in a position that keeps the suction cup distanced from the ergonomic structure 600.

In one embodiment, the insertion stem 700 is affixed to a finger rest 620 and the finger rest can be operably connected to a finger rest support 630, such as shown, by way of non-limiting example, in FIGS. 22A and 22B. In a further embodiment, the finger rest support 630 can be offset 730, such as shown, for example, in FIGS. 22A and 23. The offset positions the finger rest support on the ergonomic structure, e.g., handle 610, so that the handle, finger rest support, and hand are inhibited from contacting the face or other areas around the eye.

When extracting a contact lens from the surface of the eye, suction force can be created between the contact lens and the suction cup 220 of the over-sleeve by pressing the suction cup against the surface of the contact lens. Once adhered, the over-sleeve and suction cup can be pulled away from the eye, thereby pulling the contact lens from the surface of the eye. As detailed above, when the contact lens forms a too-strong adherence with the eye, it can be undesirable to pull the over-sleeve until the contact lens releases. It can be preferable to release the over-sleeve from the lens manipulator, allowing air to enter under the suction cup, releasing the suction and removing the suction cup from the contact lens.

Figure 19:
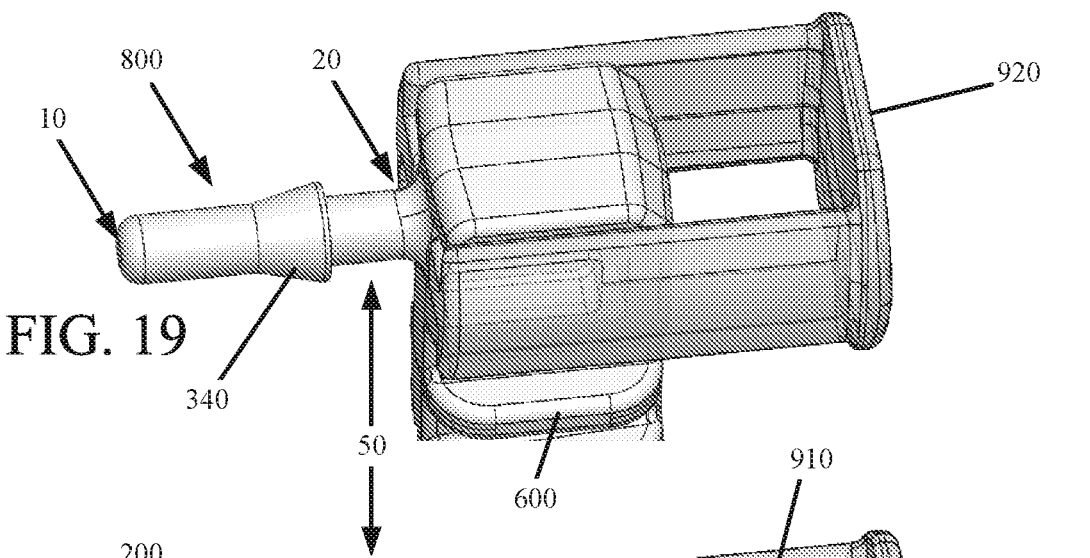
FIGS. 19, 20, and 21 illustrate one embodiment of an extraction stem with a finger-slide configured to remove an over-sleeve disposed on the extraction stem.
Figure 21:
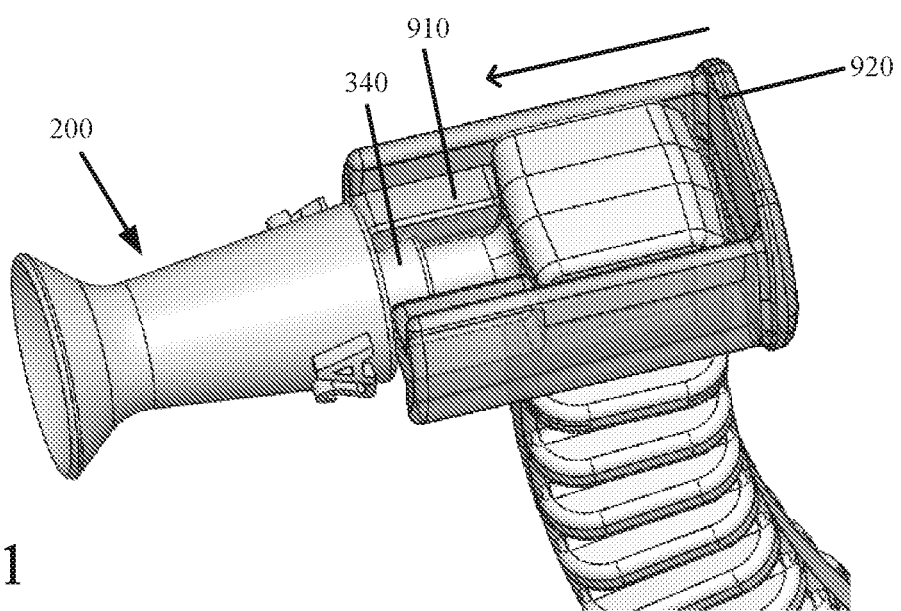

In one embodiment, an extraction stem 800 can have a friction fit with the lumen 224 of the over-sleeve, similar to that of an adjustment rod 300 with an over-sleeve. FIGS. 11, 12, 13, and 14 illustrate one non-limiting example of a lens manipulator with an extraction stem 800 that can be friction fit into an over-sleeve lumen 224. A friction fit can be facilitated by the use of a detent 340, as previously described. FIGS. 19, 21, and 24 illustrate a non-limiting example of an extraction stem 800 with a detent that is a raised shoulder that extends radially out from the extraction stem. The extraction stem and the lumen can be configured to separate if a maximum pulling force is met or exceeded when extracting a contact lens. A maximum pulling force is described above with regard to an adjustment rod and can be applicable with an extraction stem.

In one embodiment, a lens manipulator utilizes an extraction stem configured with a manual-release mechanism for pushing the over-sleeve off the extraction stem. In one embodiment, a finger slide 900 can be utilized to manually release an over-sleeve from an extraction stem. A finger-slide can be positioned distal 20 to the extraction stem, which would also place it at the distal end of an over-sleeve disposed on the extraction stem. FIGS. 8, 9, 10, 19, 20, and 21 illustrate non-limiting examples of finger-slides that can be employed on a lens manipulator to remove an over-sleeve from an extraction stem.

Figure 20:
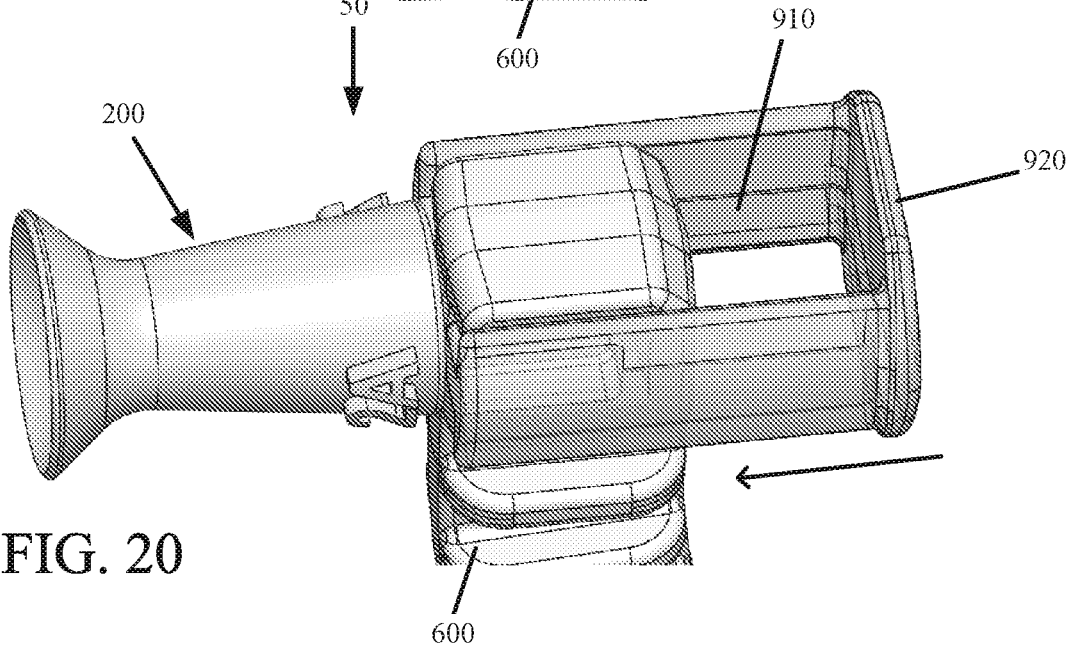

In one embodiment, a finger-slide 900 has a sliding connection 910, such as, for example, a tongue-and-groove connection, to the lens manipulator. In a more specific embodiment, the sliding connection is integrated with an ergonomic structure 600, such as a handle 610. Holding the handle allows one or more fingers to be used to push the sliding connection towards the distal end 20 of the over-sleeve, such as shown in FIGS. 19-21. In a further embodiment, the finger-slide can have a finger pad 920 at or near the distal end of the finger-slide. The finger pad can provide an area or surface against which one or more fingers can push the finger-slide towards the over-sleeve on an extraction stem. The ability to manually release the over-sleeve from the extraction stem allows the lens manipulator to be used without being calibrated or adjusted to an individual.

In a further embodiment, a detent 340 can be positioned on the extraction stem to facilitate quick removal of the over-sleeve 200 by the finger slide 900. FIGS. 19-21 illustrate a non-limiting example of an extraction stem having a detent 340 located between the proximal end 10 and the distal end 20 of the extraction stem. With this embodiment, the finger slide can be pushed towards the proximal end of the extraction stem to cause the over-sleeve to disengage from the extraction stem without the finger slide traversing the longitudinal length of the extraction stem. In other words, the finger slide can travel a shorter distance to the detent so as to disengage the over-sleeve from the extraction stem. FIGS. 20 and 21 illustrate an embodiment of the finger slide that moves proximally a sufficient distance to disengage the over-sleeve from the detent, but does not extend to the full longitudinal length of the extraction stem. This can allow the longitudinal length of the extraction stem to support the over-sleeve and quickly disengage the over-sleeve with minimal motion by the finger and the finger slide.

Placement and removal of a contact lens from the eye can be difficult for some patients. Rigid Gas Permeable lenses and hybrid lenses can provide a particular challenge because of their size and unique hard/soft configurations. The embodiments of the subject invention provide devices that make the insertion and removal of these types of lenses easier, safer, and minimize the possibility of damage to the eye. A lens manipulator of the subject invention can be configured with sufficient suction force to hold a contact lens in place, on the suction cup, during insertion and still release from the contact lens after insertion. A lens manipulator of the subject invention can also include a safety release feature that releases the suction cup from the contact lens if the contact lens cannot be removed from the eye or if the suction cup cannot be removed from the contact lens.

All patents, patent applications, provisional applications, and other publications referred to or cited herein are incorporated by reference in their entirety, including all figures and tables, to the extent they are not inconsistent with the explicit teachings of this specification. Additionally, the entire contents of the references cited within the references cited herein are also entirely incorporated by reference.

The examples and embodiments described herein are for illustrative purposes only and that various modifications or changes in light thereof will be suggested to persons skilled in the art and are to be included within the spirit and purview of this application.

Any reference in this specification to "one embodiment," "an embodiment," "example embodiment," "further embodiment," "alternative embodiment," etc., is for literary convenience. The implication is that any particular feature, structure, or characteristic described in connection with such an embodiment is included in at least one embodiment of the invention. The appearance of such phrases in various places in the specification does not necessarily refer to the same embodiment. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

What is claimed is:

1. A lens manipulator comprising:
    an over-sleeve with a continuous lumen therethrough that terminates in a pore that opens onto a suction cup at a proximal end and a rod opening at a distal end;
    an extraction stem removably insertable into the lumen through the rod opening to thereby form a friction fit that closes the lumen and allows the suction cup to create a suction force;
    an insertion stem removably insertable into the lumen through the rod opening, having a vent along a longitudinal length of the insertion stem that inhibits formation of a suction force under the suction cup; and
    an ergonomic structure on which the extraction stem and insertion stem are operably affixed, such that when the extraction stem is removably inserted into the lumen of the over-sleeve, the lens manipulator is functional to remove a contact lens and when the insertion stem is removably inserted into the lumen of the over-sleeve, the lens manipulator is functional to insert a contact lens.

2. The lens manipulator according to claim 1, wherein the suction force formed by the suction cup with a contact lens is adjustable from between approximately 100 grams and 150 grams.

3. The lens manipulator according to claim 2, wherein the suction force formed by the suction cup with a contact lens is adjustable from between approximately 110 grams and approximately 140 grams.

4. The lens manipulator according to claim 3, wherein the suction force formed by the suction cup with a contact lens is approximately 130 grams.

5. The lens manipulator according to claim 1, wherein the suction cup is off-set, such that the apex is off-center from a longitude length of at least one of the extraction stem and the insertion stem.

6. The lens manipulator according to claim 1, further comprising a detent on the insertion stem that engages with the lumen to removably secure the over-sleeve.

7. The lens manipulator according to claim 1, wherein the over-sleeve is at least partially removable from the extraction stem when a maximum pulling force is exerted against the suction force under the suction cup.

8. The lens manipulator according to claim 7, wherein the maximum pulling force is between approximately 100 grams and approximately 150 grams.

9. The lens manipulator according to claim 8, further comprising a detent on the extraction stem.

10. The lens manipulator according to claim 1, wherein at least one of the extraction stem and the insertion stem is non-collinear with a longitudinal length of the ergonomic structure.

11. The lens manipulator according to claim 10, wherein the ergonomic structure is a handle for controlling and manipulating the over-sleeve.

12. The lens manipulator according to claim 11, wherein the extraction stem is at one end of the handle and the insertion stem is at another end of the handle.

13. The lens manipulator according to claim 1, further comprising a manual-release mechanism for disengaging the over-sleeve from the extraction stem, so as to release any suction force under the suction cup.

14. The lens manipulator according to claim 13, wherein the manual-release mechanism comprises a finger-slide, such that, when the finger-slide is advanced towards the over-sleeve, the extraction stem disengages with the lumen, thereby releasing the suction force under the suction cup.

15. The lens manipulator according to claim 14, wherein the suction force is released when the over-sleeve is partially disengaged from the extraction stem.

16. The lens manipulator according to claim 14, wherein the finger-slide is configured to be manipulated with a finger.

17. A method for utilizing a lens manipulator, according to claim 1, adapted to manipulate a contact lens, comprising:
    positioning the lens manipulator, with the over-sleeve engaged with the insertion stem, so that the suction cup can receive a contact lens thereon;
    filling the concavity of the contact lens with a solution;
    advancing the over-sleeve towards a desired location until the contact lens releases from the suction cup and attaches to the desired location; and
    moving the lens manipulator with the over-sleeve away from the desired location.

18. The method according to claim 17, further comprising:

positioning the lens manipulator, with the over-sleeve engaged with the extraction stem, so that the suction cup is in contact with a contact lens at the desired location;

pressing the suction cup against the contact lens until a suction force is formed under the suction cup, thereby attaching the contact lens to the suction cup; and moving the lens manipulator away from the desired location to disengage the contact lens from the desired location.

19. The method according to claim 18, further comprising a manual-release mechanism on the lens manipulator and the method further comprises advancing the manual-release mechanism towards the over-sleeve to disengage the over-sleeve from the extraction stem, thereby releasing the suction force so that the lens manipulator is moveable from the desired location.

20. A kit, configured to manipulate a contact lens, comprising:

a lens manipulator, according to claim 1; and a solution for use with a contact lens.

21. The kit according to claim 20, further comprising at least one additional over-sleeve.

* * * * *